US011324873B2

(12) United States Patent
Gilmanshin et al.

(10) Patent No.: US 11,324,873 B2
(45) Date of Patent: May 10, 2022

(54) ACOUSTIC BLOOD SEPARATION PROCESSES AND DEVICES

(71) Applicant: FloDesign Sonics, Inc., West Springfield, MA (US)

(72) Inventors: Rudolf Gilmanshin, Framingham, MA (US); Bart Lipkens, Hampden, MA (US); Brian Dutra, East Longmeadow, MA (US); Daniel Kennedy, Longmeadow, MA (US)

(73) Assignee: FloDesign Sonics, Inc., West Springfield, MA (US)

( * ) Notice: Subject to any disclaimer, the term of this patent is extended or adjusted under 35 U.S.C. 154(b) by 193 days.

(21) Appl. No.: 15/257,515

(22) Filed: Sep. 6, 2016

(65) Prior Publication Data

US 2017/0049949 A1 Feb. 23, 2017

Related U.S. Application Data

(63) Continuation-in-part of application No. 13/866,584, filed on Apr. 19, 2013, now Pat. No. 10,201,652.
(Continued)

(51) Int. Cl.
*A61M 1/36* (2006.01)
*B01D 21/34* (2006.01)
(Continued)

(52) U.S. Cl.
CPC ......... *A61M 1/3678* (2014.02); *B01D 21/286* (2013.01); *B01D 21/30* (2013.01);
(Continued)

(58) Field of Classification Search
CPC .............. A61M 1/3678; A61M 1/3693; B01D 11/0265; B01D 11/0261; B01D 43/00
See application file for complete search history.

(56) References Cited

U.S. PATENT DOCUMENTS 2,473,971 A 6/1949 Ross
2,667,944 A 2/1954 Crites
(Continued)

FOREIGN PATENT DOCUMENTS

DE 30 27 433 A1 2/1982
DE 196 48 519 A1 6/1998
(Continued)

OTHER PUBLICATIONS

Lipkens et al. "Separation of bacterial spores from flowing water in macro-scale cavities by ultrasonic standing waves." (Article uploaded to arXiv: Jun. 2010, http://arxiv.org/abs/1006.5467). (Year: 2010).*
(Continued)

*Primary Examiner* — Ryan B Huang
(74) *Attorney, Agent, or Firm* — FloDesign Sonics, Inc.

(57) ABSTRACT

Acoustophoretic devices are disclosed. The devices include a flow chamber, an ultrasonic transducer, a reflector, an inlet, a filtrate outlet, a concentrate outlet, and optionally a lipid collection trap. The ultrasonic transducer and reflector create a multi-dimensional acoustic standing wave in the flow chamber that traps and separates red blood cells and/or lipids from blood. Concentrated red blood cells can be recovered via the concentrate outlet, the lipids can be recovered via the lipid collection trap, and the remaining blood can be recovered via the filtrate outlet. Methods for separating blood components (e.g., red blood cells, lipids, platelets, white blood cells) from blood are also disclosed. The red blood cells can undergo washing with a solvent to remove undesired admixtures. Cryoprotectants can be added or removed from the blood.

6 Claims, 20 Drawing Sheets

Related U.S. Application Data

(60) Provisional application No. 62/371,829, filed on Aug. 7, 2016, provisional application No. 62/214,567, filed on Sep. 4, 2015, provisional application No. 61/636,515, filed on Apr. 20, 2012.

(51) Int. Cl.
*B01D 21/28* (2006.01)
*B06B 1/06* (2006.01)
*B01D 21/30* (2006.01)

(52) U.S. Cl.
CPC ............ *B01D 21/34* (2013.01); *B06B 1/0644* (2013.01); *A61M 2202/0427* (2013.01); *A61M 2202/0429* (2013.01); *A61M 2202/0439* (2013.01); *A61M 2202/0456* (2013.01); *B01D 2221/10* (2013.01)

(56) References Cited

U.S. PATENT DOCUMENTS

| | | |
|---|---|---|
| 3,372,370 A | 3/1968 | Cyr |
| 3,555,311 A | 1/1971 | Weber |
| 4,055,491 A | 10/1977 | Porath-Furedi |
| 4,065,875 A | 1/1978 | Srna |
| 4,118,649 A | 10/1978 | Schwartzman et al. |
| 4,158,629 A | 6/1979 | Sawyer |
| 4,165,273 A | 8/1979 | Azarov et al. |
| 4,173,725 A | 11/1979 | Asai et al. |
| 4,204,096 A | 5/1980 | Barcus et al. |
| 4,320,659 A | 3/1982 | Lynnworth et al. |
| 4,344,448 A | 8/1982 | Potts |
| 4,398,325 A | 8/1983 | Piaget et al. |
| 4,666,595 A | 5/1987 | Graham |
| 4,699,588 A | 10/1987 | Zinn et al. |
| 4,743,361 A | 5/1988 | Schram |
| 4,759,775 A | 7/1988 | Peterson et al. |
| 4,800,316 A | 1/1989 | Wang |
| 4,821,838 A | 4/1989 | Chen |
| 4,836,684 A | 6/1989 | Javorik et al. |
| 4,878,210 A | 10/1989 | Mitome |
| 4,983,189 A | 1/1991 | Peterson et al. |
| 5,164,094 A | 11/1992 | Stuckart |
| 5,225,089 A | 7/1993 | Benes et al. |
| 5,371,729 A | 12/1994 | Manna |
| 5,395,592 A | 3/1995 | Bolleman et al. |
| 5,431,817 A | 7/1995 | Braatz et al. |
| 5,443,985 A | 8/1995 | Lu et al. |
| 5,452,267 A | 9/1995 | Spevak |
| 5,484,537 A | 1/1996 | Whitworth |
| 5,527,460 A | 6/1996 | Trampler et al. |
| 5,560,362 A | 10/1996 | Sliwa, Jr. et al. |
| 5,594,165 A | 1/1997 | Madanshetty |
| 5,604,301 A | 2/1997 | Mountford et al. |
| 5,626,767 A | 5/1997 | Trampler et al. |
| 5,688,405 A | 11/1997 | Dickinson et al. |
| 5,711,888 A | 1/1998 | Trampler et al. |
| 5,831,166 A | 11/1998 | Kozuka et al. |
| 5,834,871 A | 11/1998 | Puskas |
| 5,902,489 A | 5/1999 | Yasuda et al. |
| 5,912,182 A | 6/1999 | Coakley et al. |
| 5,951,456 A | 9/1999 | Scott |
| 6,090,295 A | 6/2000 | Raghavarao et al. |
| 6,166,231 A | 12/2000 | Hoeksema |
| 6,216,538 B1 | 4/2001 | Yasuda et al. |
| 6,205,848 B1 | 6/2001 | Faber et al. |
| 6,273,262 B1 | 8/2001 | Yasuda et al. |
| 6,332,541 B1* | 12/2001 | Coakley .................. B01J 19/10 209/18 |
| 6,391,653 B1 | 5/2002 | Letcher et al. |
| 6,482,327 B1 | 11/2002 | Mori et al. |
| 6,487,095 B1 | 11/2002 | Malik et al. |
| 6,592,821 B1 | 7/2003 | Wada et al. |
| 6,595,989 B1* | 7/2003 | Schaer .................. A61B 18/1492 606/41 |
| 6,649,069 B2 | 11/2003 | DeAngelis |
| 6,699,711 B1 | 3/2004 | Hahn et al. |
| 6,763,722 B2 | 7/2004 | Fjield et al. |
| 6,881,314 B1 | 4/2005 | Wang et al. |
| 6,929,750 B2 | 8/2005 | Laurell et al. |
| 6,936,151 B1 | 8/2005 | Lock et al. |
| 7,008,540 B1 | 3/2006 | Weavers et al. |
| 7,010,979 B2 | 3/2006 | Scott |
| 7,061,163 B2 | 6/2006 | Nagahara et al. |
| 7,081,192 B1 | 7/2006 | Wang et al. |
| 7,093,482 B2 | 8/2006 | Berndt |
| 7,108,137 B2 | 9/2006 | Lal et al. |
| 7,150,779 B2 | 12/2006 | Meegan, Jr. |
| 7,186,502 B2 | 3/2007 | Vesey |
| 7,191,787 B1 | 3/2007 | Redeker et al. |
| 7,322,431 B2 | 1/2008 | Ratcliff |
| 7,331,233 B2 | 2/2008 | Scott |
| 7,340,957 B2 | 3/2008 | Kaduchak et al. |
| 7,373,805 B2 | 5/2008 | Hawkes et al. |
| 7,541,166 B2 | 6/2009 | Belgrader et al. |
| 7,601,267 B2 | 10/2009 | Haake et al. |
| 7,673,516 B2 | 3/2010 | Janssen et al. |
| 7,837,040 B2 | 11/2010 | Ward et al. |
| 7,846,382 B2 | 12/2010 | Strand et al. |
| 7,968,049 B2 | 6/2011 | Takahashi et al. |
| 8,080,202 B2 | 12/2011 | Takahashi et al. |
| 8,134,705 B2 | 3/2012 | Kaduchak et al. |
| 8,256,076 B1 | 9/2012 | Feller |
| 8,266,950 B2 | 9/2012 | Kaduchak et al. |
| 8,273,253 B2 | 9/2012 | Curran |
| 8,273,302 B2 | 9/2012 | Takahashi et al. |
| 8,309,408 B2 | 11/2012 | Ward et al. |
| 8,319,398 B2 | 11/2012 | Vivek et al. |
| 8,334,133 B2 | 12/2012 | Fedorov et al. |
| 8,387,803 B2 | 3/2013 | Thorslund et al. |
| 8,592,204 B2 | 11/2013 | Lipkens et al. |
| 8,679,338 B2 | 3/2014 | Rietman et al. |
| 8,691,145 B2 | 4/2014 | Dionne et al. |
| 8,873,051 B2 | 10/2014 | Kaduchak et al. |
| 8,889,388 B2 | 11/2014 | Wang et al. |
| 2002/0038662 A1 | 4/2002 | Schuler et al. |
| 2002/0134734 A1 | 9/2002 | Campbell et al. |
| 2003/0015035 A1* | 1/2003 | Kaduchak ............ B01D 49/006 73/570.5 |
| 2003/0028108 A1 | 2/2003 | Miller et al. |
| 2003/0195496 A1 | 10/2003 | Maguire |
| 2003/0209500 A1 | 11/2003 | Kock et al. |
| 2003/0221561 A1* | 12/2003 | Milo ................ A61B 17/22012 96/175 |
| 2003/0230535 A1 | 12/2003 | Affeld et al. |
| 2004/0016699 A1 | 1/2004 | Bayevsky |
| 2004/0069708 A1* | 4/2004 | Laurell ............... A61M 1/3472 210/646 |
| 2005/0031499 A1 | 2/2005 | Meier |
| 2005/0121269 A1 | 6/2005 | Namduri |
| 2005/0145567 A1 | 7/2005 | Quintel et al. |
| 2005/0196725 A1 | 9/2005 | Fu |
| 2006/0037915 A1* | 2/2006 | Strand ............... B01L 3/502761 210/748.05 |
| 2006/0037916 A1 | 2/2006 | Trampler |
| 2007/0272618 A1 | 11/2007 | Gou et al. |
| 2007/0284299 A1 | 12/2007 | Xu et al. |
| 2008/0105625 A1 | 5/2008 | Rosenberg et al. |
| 2008/0181828 A1* | 7/2008 | Kluck .................... B01D 21/34 422/128 |
| 2008/0217259 A1* | 9/2008 | Siversson ........... A61M 1/3693 436/177 |
| 2008/0245709 A1 | 10/2008 | Kaduchak et al. |
| 2008/0272034 A1 | 11/2008 | Ferren et al. |
| 2008/0272065 A1 | 11/2008 | Johnson |
| 2009/0029870 A1 | 1/2009 | Ward et al. |
| 2009/0053686 A1 | 2/2009 | Ward et al. |
| 2009/0087492 A1 | 4/2009 | Johnson et al. |
| 2009/0098027 A1 | 4/2009 | Tabata et al. |
| 2009/0104594 A1 | 4/2009 | Webb |
| 2009/0178716 A1 | 7/2009 | Kaduchak et al. |
| 2009/0194420 A1 | 8/2009 | Mariella, Jr. et al. |
| 2009/0045107 A1 | 12/2009 | Ward et al. |
| 2009/0295505 A1 | 12/2009 | Mohammadi et al. |

(56) References Cited

U.S. PATENT DOCUMENTS

| | | |
|---|---|---|
| 2010/0000945 A1 | 1/2010 | Gavalas |
| 2010/0078323 A1 | 4/2010 | Takahashi et al. |
| 2010/0078384 A1 | 4/2010 | Yang |
| 2010/0124142 A1 | 5/2010 | Laugharn et al. |
| 2010/0139377 A1 | 6/2010 | Huang et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0261918 A1 | 10/2010 | Chianelli et al. |
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0003350 A1 | 1/2011 | Schafran et al. |
| 2011/0024335 A1 | 2/2011 | Ward et al. |
| 2011/0092726 A1 | 4/2011 | Clarke |
| 2011/0095225 A1 | 4/2011 | Eckelberry et al. |
| 2011/0123392 A1* | 5/2011 | Dionne .................. A61L 2/025 422/1 |
| 2011/0125024 A1 | 5/2011 | Mueller |
| 2011/0146678 A1 | 6/2011 | Ruecroft et al. |
| 2011/0154890 A1* | 6/2011 | Holm .................. B01D 21/283 73/61.75 |
| 2011/0166551 A1 | 7/2011 | Schafer |
| 2011/0189732 A1 | 8/2011 | Weinand et al. |
| 2011/0262990 A1 | 10/2011 | Wang et al. |
| 2011/0278218 A1 | 11/2011 | Dionne et al. |
| 2011/0281319 A1 | 11/2011 | Swayze et al. |
| 2011/0284475 A1* | 11/2011 | Kolodny ................. C02F 1/004 210/748.02 |
| 2011/0309020 A1 | 12/2011 | Rietman et al. |
| 2012/0088295 A1 | 4/2012 | Yasuda et al. |
| 2012/0163126 A1 | 6/2012 | Campbell et al. |
| 2012/0175012 A1 | 7/2012 | Goodwin et al. |
| 2012/0267288 A1 | 10/2012 | Chen et al. |
| 2012/0325727 A1 | 12/2012 | Dionne et al. |
| 2012/0325747 A1 | 12/2012 | Reitman et al. |
| 2012/0328477 A1 | 12/2012 | Dionne et al. |
| 2012/0329122 A1 | 12/2012 | Lipkens et al. |
| 2013/0115664 A1 | 5/2013 | Khanna et al. |
| 2013/0175226 A1* | 7/2013 | Coussios .............. B01D 21/283 210/748.05 |
| 2013/0217113 A1 | 8/2013 | Srinivasan et al. |
| 2013/0277316 A1 | 10/2013 | Dutra et al. |
| 2013/0277317 A1 | 10/2013 | LoRicco et al. |
| 2013/0284271 A1 | 10/2013 | Lipkens et al. |
| 2014/0011240 A1 | 1/2014 | Lipkens et al. |
| 2014/0017758 A1 | 1/2014 | Kniep et al. |
| 2014/0319077 A1 | 10/2014 | Lipkens et al. |

FOREIGN PATENT DOCUMENTS

| | | | |
|---|---|---|---|
| DE | 10 2008 006 501 A1 | 9/2008 | |
| EP | 0 292 470 B1 | 11/1988 | |
| EP | 1 254 669 B1 | 11/2002 | |
| GB | 2 420 510 A | 5/2006 | |
| JP | 9-136090 | 5/1997 | |
| WO | WO 1987/07178 A1 | 12/1987 | |
| WO | WO 90/05008 | 3/1990 | |
| WO | WO 98/50133 A1 | 11/1998 | |
| WO | WO 02/072234 A1 | 9/2002 | |
| WO | WO 2004/079716 A1 | 9/2004 | |
| WO | WO 2009/111276 A1 | 9/2009 | |
| WO | WO 2009/144709 A1 | 12/2009 | |
| WO | WO 2010/024753 A1 | 4/2010 | |
| WO | WO 2010/040394 A1 | 4/2010 | |
| WO | WO 2011/023949 A2 | 3/2011 | |
| WO | WO 2011/025890 A1 | 3/2011 | |
| WO | WO 2011/027146 A2 | 3/2011 | |
| WO | WO-2011027146 A2 * | 3/2011 | ......... B01D 21/0009 |
| WO | WO 2011/131947 A2 | 10/2011 | |
| WO | WO 2011/161463 A2 | 12/2011 | |
| WO | WO 2013/043297 A1 | 3/2013 | |
| WO | WO 2013/055517 A1 | 4/2013 | |
| WO | WO 2013/159014 A1 | 10/2013 | |
| WO | WO 2014/014941 A1 | 1/2014 | |
| WO | WO 2014/055219 A2 | 4/2014 | |
| WO | WO 2014/124306 A1 | 8/2014 | |

OTHER PUBLICATIONS

Petersson, Filip. "On acoustic particle and cell manipulation in microfluidic systems" (PhD Thesis, Lund University, Apr. 2007). (Year: 2007).*

Alvarez et al.; ShockWaves, vol. 17, No. 6, pp. 441-447, 2008.

Benes et al.; Ultrasonic Separation of Suspended Particles, 2001 IEEE Ultrasonics Symposium; Oct. 7-10, 2001; pp. 649-659; Atlanta, Georgia.

Castro; Tunable gap and quantum quench dynamics in bilayer graphene; Jul. 13, 2010; Mathematica Summer School.

Cravotto et al.; Ultrasonics Sonochemistry, vol. 15, No. 5, pp. 898-902, 2008.

Garcia-Lopez, et al.; Enhanced Acoustic Separation of Oil-Water Emulsion in Resonant Cavities. The Open Acoustics Journal. 2008, vol. 1, pp. 66-71.

Hill et al.; Ultrasonic Particle Manipulation; Microfluidic Technologies for Miniaturized Analysis Systems, Jan. 2007, pp. 359-378.

Ilinskii et al.; Acoustic Radiation Force on a Sphere in Tissue; AIP Conference Proceedings; 2012.

Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.

Latt et al.; Ultrasound-membrane hybrid processes for enhancement of filtration properties; Ultrasonics sonochemistry 13.4 (2006): 321-328.

Lipkens et al.; Frequency sweeping and fluid flow effects on particle trajectories in ultrasonic standing waves; Acoustics 08, Paris, Jun. 29-Jul. 4, 2008.

Lipkens et al.; Prediction and measurement of particle velocities in ultrasonic standing waves; J. Acoust. Soc. Am., 124 No. 4, p. 2492 (A) 2008.

Lipkens et al.; Separation of micron-sized particles in macro-scale cavities by ultrasonic standing waves; Presented at the International Congress on Ultrasonics, Santiago; Jan. 11-17, 2009.

Lipkens et al.; The effect of frequency sweeping and fluid flow on particle trajectories in ultrasonic standing waves; IEEE Sensors Journal, vol. 8, No. 6, pp. 667-677, 2008.

Lipkens et al., Macro-scale acoustophoretic separation of lipid particles from red blood cells, The Journal of the Acoustical Society of America, vol. 133, Jun. 2, 2013, p. 045017, XP055162509, New York, NY.

Meribout et a.; An Industrial-Prototype Acoustic Array for Real-Time Emulsion Layer Detection in Oil Storage Tanks; IEEE Sensors Journal, vol. 9, No. 12, Dec. 2009.

Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.

Pangu et al.; Droplet transport and coalescence kinetics in emulsions subjected to acoustic fields; Ultrasonics 46, pp. 289-302 (2007).

Ponomarenko et al.; Density of states and zero Landau level probed through capacitance of graphene; Nature Nanotechnology Letters, Jul. 5, 2009; DOI: 10.1038/NNAN0.2009.177.

Seymour et al., J. Chem. Edu., 1990, 67(9), p. 763, published Sep. 1990.

Wang et al.; Retention and Viability Characteristics of Mammalian Cells in an Acoustically Driven Polymer Mesh; Biotechnol. Prog. 2004, pp. 384-387 (2004).

Annex to Form PCT/ISA/206—Communication Relating to the Results of the Partial International Search Report, dated Jul. 18, 2013.

(56) References Cited

OTHER PUBLICATIONS

European Search Report of European Application No. 11769474.5, dated Sep. 5, 2013.
European Search Report of European Application No. 13760840.2, dated Feb. 4, 2016.
International Search Report and Written Opinion dated Dec. 20, 2011, for corresponding PCT application No. PCT/US2011/032181.
International Search Report and Written Opinion dated Feb. 27, 2012, for PCT application No. PCT/US2011/040787.
International Search Report and Written Opinion of International Application No. PCT/US2012/051804 dated Nov. 16, 2012.
International Search Report and Written Opinion of International Application No. PCT/US2013/037404 dated Jun. 21, 2013.
International Search Report and Written Opinion of International Application No. PCT/US2013/032705 dated Jul. 26, 2013.
International Search Report and Written Opinion of International Application No. PCT/US2013/050729 dated Sep. 25, 2013.
International Search Report dated Feb. 18, 2014 in corresponding PCT Application No. PCT/US2013/059640.
International Search Report for corresponding PCT Application Serial No. PCT/US2014/015382 dated May 6, 2014.
International Search Report for PCT/US2014/035557 dated Aug. 27, 2014.
International Search Report for PCT/US2014/043930 dated Oct. 22, 2014.
International Search Report for PCT/US2014/046412 dated Oct. 27, 2014.
International Search Report for PCT/US2014/064088 dated Jan. 30, 2015.
Extended European Search Report for Application No. EP 12833859.7 dated Mar. 20, 2015.
International Search Report and Written Opinion for International Application No. PCT/US2015/010595 dated Apr. 15, 2015.
International Search Report for PCT/US2015/019755 dated May 4, 2015.
International Search Report dated Jul. 30, 2015 for International Application No. PCT/US2015/030009.
International Search Report for PCT/US2015/039125 dated Sep. 30, 2015.
European Search Report of European Application No. 11796470.0 dated Jan. 5, 2016.
International Search Report and Written Opinion for International Application No. PCT/US2015/066884, dated Mar. 22, 2016.
International Search Report and Written Opinion for International Application No. PCT/US2016/024082 dated Jun. 27, 2016.
Phys. Org. "Engineers develop revolutionary nanotech water desalination membrane." Nov. 6, 2006. http://phys.org/news82047372.html.
"Proceedings of the Acoustics 2012 Nantes Conference," Apr. 23-27, 2012, Nantes, France, pp. 278-282.
Sony New Release: <http://www.sony.net/SonyInfo/News/Press/201010/10-137E/index.html>.
Lipkens et al.; "Macro-scale acoustophoretic separation of lipid particles . . . "; The Journal of the Acoustical Society of America; vol. 133, p. 045107; Jun. 2, 2013.
International Search Report and Written Opinion for International Application No. PCT/US2016/050415, dated Nov. 28, 2016.

* cited by examiner

% Red Blood Cells Retained

| $\dot{V}_f / \dot{V}_c$ | 10 | 20 | 30 | 45 | 60 |
|---|---|---|---|---|---|
| 5 | 85% | 84% | 60% | 40% | 45% |
| 4 | 99% | 91% | 69% | 55% | 47% |
| 3 | 97% | 88% | 76% | 55% | 62% |
| 2 | 92% | 89% | 70% | 73% | 55% |
| 1 | 101% | 86% | 78% | 78% | 76% |
| | \multicolumn{5}{c}{$\dot{V}_{in}$ (mL/min)} |

FIG. 6A

RBC Concentration Factor

| $\dot{V}_f / \dot{V}_c$ | 10 | 20 | 30 | 45 | 60 |
|---|---|---|---|---|---|
| 5 | 5.4 | 4.9 | 3.3 | 2.4 | 2.7 |
| 4 | 5.3 | 4.6 | 3.4 | 2.7 | 2.3 |
| 3 | 4.4 | 3.6 | 3.1 | 2.2 | 2.5 |
| 2 | 2.9 | 2.8 | 2.3 | 2.3 | 1.6 |
| 1 | 2.0 | 1.7 | 1.5 | 1.7 | 1.6 |
| | \multicolumn{5}{c}{$\dot{V}_{in}$ (mL/min)} |

FIG. 6B

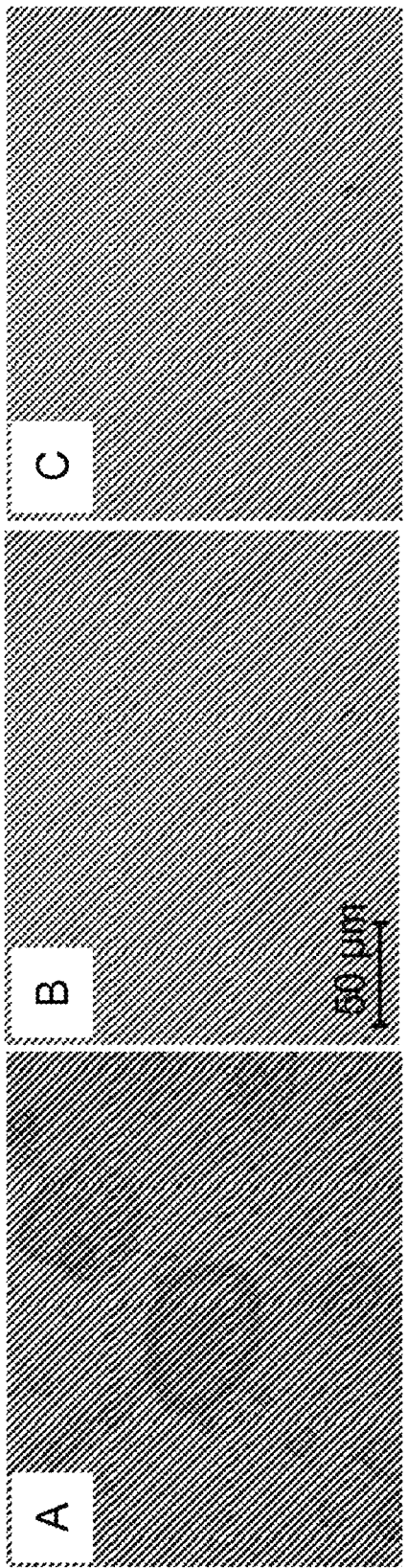
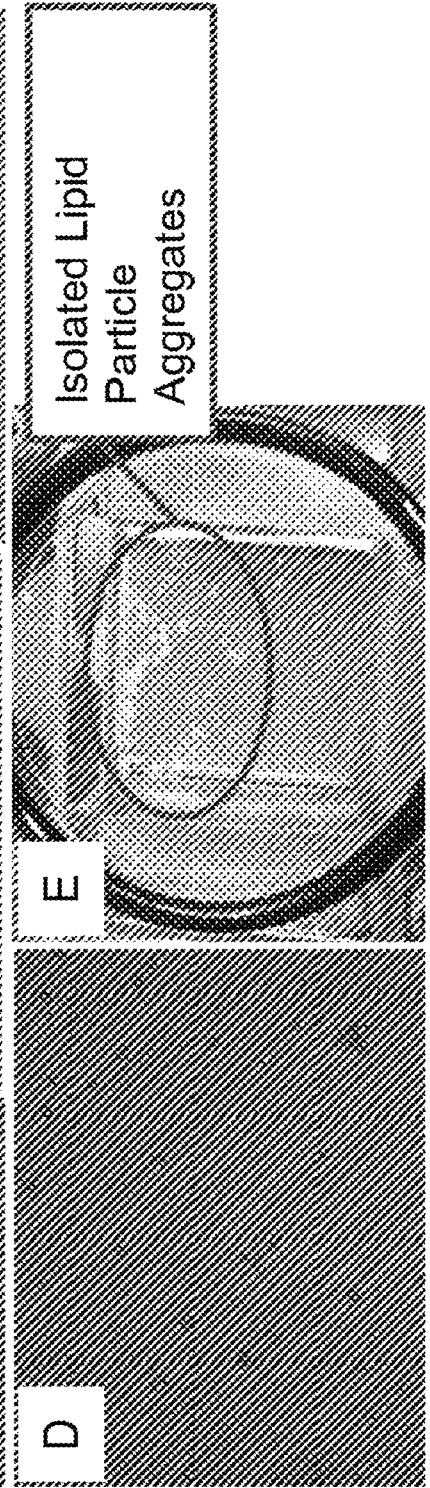
FIG. 7A  FIG. 7B  FIG. 7C
FIG. 7D  FIG. 7E
Isolated Lipid Particle Aggregates

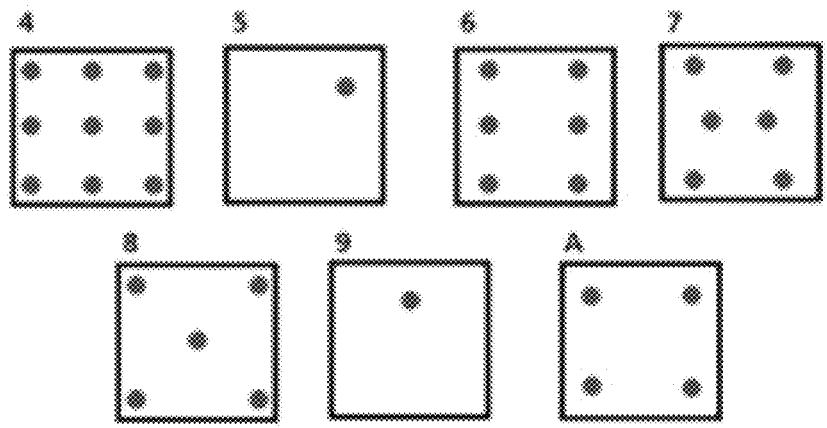
FIG. 20A
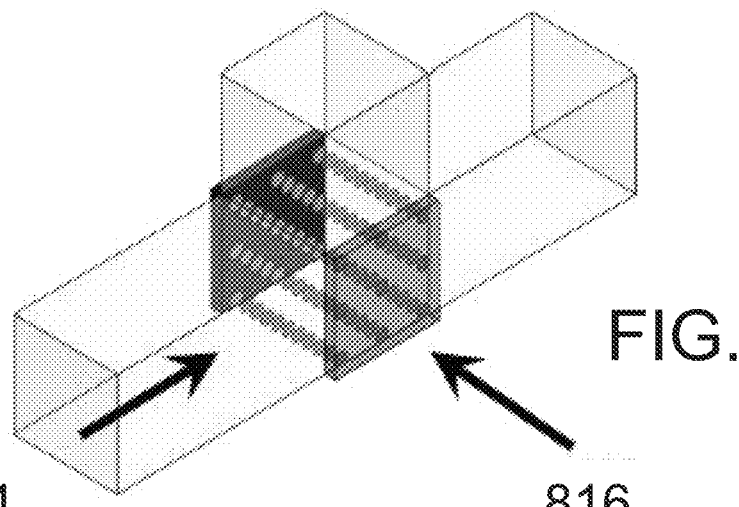
FIG. 20B
814    816
FIG. 20C
FIG. 20D
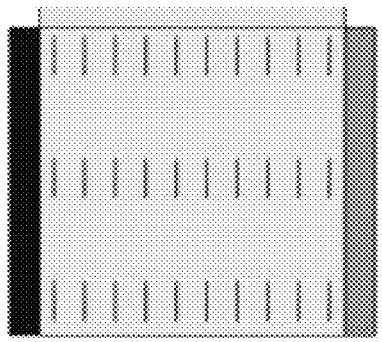
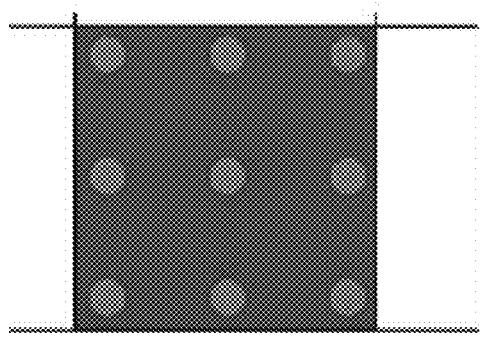

ACOUSTIC BLOOD SEPARATION PROCESSES AND DEVICES

CROSS-REFERENCE TO RELATED APPLICATIONS

This application claims priority to U.S. Provisional Patent Application Ser. No. 62/214,567, filed on Sep. 4, 2015 and to U.S. Provisional Patent Application Ser. No. 62/371,829, filed on Aug. 7, 2016; and is also a continuation-in-part of U.S. patent application Ser. No. 13/866,584, filed on Apr. 19, 2013, which claimed priority to U.S. Provisional Patent Application Ser. No. 61/636,515, filed on Apr. 20, 2012, the disclosures of which are hereby fully incorporated herein by reference in their entireties.

BACKGROUND

Cardiopulmonary bypass surgery is a common procedure whereby the function of the heart and lungs are taken over by a pump system commonly called a heart-lung machine. Cardiopulmonary bypass surgery is commonly used in coronary bypass heart surgery due to the difficulty of operating on a beating heart. This surgical procedure is also used for the repair of cardiac valves, organ transplants, repair of large aneurysms, and other life-saving procedures. One of the issues associated with cardiopulmonary bypass surgery is injury to the patient due to strokes caused by micro-emboli. These microemboli are many times caused by lipids that result from the incision into the thoracic cavity through the sternum. Sternal bone marrow contains a large amount of lipids. The lipids wash into the pool of pericardial blood from the sternum and the incision through several tissues, particularly the large amount of fat that is found in the stomach of older patients. This blood is often scavenged with a suction line and returned to the patient through the heart-lung machine. Perioperative use of the patient's own blood is a common practice in cardiac, trauma, and orthopedic surgery.

The use of filters, centrifuges and other separation devices are currently used for separating deleterious lipids generated during surgery. Some of the drawbacks of these devices are the expense for operation, the cleaning of these devices, the cost of the disposables involved, the efficacy of the filtration process, and the viability of the cells after going through some of the separation processes. For example, a centrifuge at high revolutions will cause the destruction of many of the components of blood. Lipid particles show a size distribution of approximately 5 micrometers (µm) to 70 µm in diameter, with most particles being ≤10 µm. This is about the same size as red blood cells. Typical filters have a pore size of 25 µm to 40 µm, and a lipid removal efficiency of only 30% to 40%. Also, filters clog and suffer from throughput constraints, are replaced in practice, potentially multiple times, and may break up larger droplets into smaller droplets. Centrifugation is time-consuming, expensive, and is implemented using trained personnel. Also, the high speeds used for centrifugation may damage the blood cells, and removes beneficial blood components such as platelets and clotting factors. As previously mentioned, some MEMS devices have been used, but rely on very small passages that essentially "line up" red blood cells and lipid particles for separation. This process results in very low throughput, and cannot handle large amounts in bulk. Additionally, these devices and methods also suffer from limitations of potential fragmentation and deformation of red blood cells (RBCs), and the potential to activate clotting or inflammatory cascades. Moreover, the time to process the blood in these devices, which work in a "batch" mode, prevents the immediate re-transfusion of blood to the patient.

In addition, the separation of blood components in the blood has a number of applications. For example, various blood components, such as red blood cells (erythrocytes), white blood cells (leukocytes), and platelets are used in various therapeutic operations in their separated form.

BRIEF DESCRIPTION

The present disclosure relates, in various embodiments, to acoustophoretic devices with improved fluid dynamics that can be used to improve the separation of blood components and/or lipids from blood. More particularly, the devices include a flow chamber containing an ultrasonic transducer and reflector that set up a multi-dimensional acoustic standing wave.

Disclosed herein are acoustophoresis devices for separating components (e.g., red blood cells (RBCs), white blood cells (leukocytes), platelets, lipids) from blood (e.g., during surgery). The device comprises a flow chamber through which is flowed blood containing blood components, an ultrasonic transducer positioned on a wall of the flow chamber and a reflector located on a wall of the flow chamber opposite the ultrasonic transducer, an inlet on a first side of the flow chamber; a filtrate outlet; and a concentrate outlet below the acoustic standing wave. The ultrasonic transducer includes a piezoelectric material driven by a voltage signal to create a multi-dimensional acoustic standing wave in the acoustic chamber.

In particular constructions, the filtrate outlet is located above the acoustic standing wave. In other alternative constructions, the flow chamber further comprises a lipid collection trap above the acoustic standing wave, and the filtrate outlet is located on a second side of the flow chamber opposite the first side thereof. The flow chamber can further comprise a shallow wall tapered from the filtrate outlet to the concentrate outlet.

In certain embodiments, the device can further comprise a container (e.g., bag) detachably connected to the concentrate outlet. The container can be configured to automatically seal upon detachment from the concentrate outlet without comprising the sterility of any material held within the container. The container may be a disposable bag capable of withstanding temperatures from about −80° C. to about 40° C.

The flow chamber can have an interior volume of at least 50 mL.

Also disclosed herein is a portable, autonomous system comprising an acoustophoretic device according to the present disclosure that is battery-powered.

Also disclosed in various embodiments herein are methods for separating components (e.g., red blood cells (RBCs), white blood cells (leukocytes), platelets, lipids) from blood (e.g., surgical blood). The method comprises flowing the blood through a flow chamber and driving the ultrasonic transducer by a voltage signal to generate a multi-dimensional acoustic standing wave in the blood, wherein each acoustic standing wave exerts an acoustic radiation force, such that blood components, such as, for example, the red blood cells, are trapped in the acoustic standing wave against fluid drag force.

The blood can be undiluted whole blood and can be flowed through the flow chamber at a flow rate of at least two liters per hour. The trapped red blood cells may coalesce or agglomerate such that they are separated through enhanced gravitational settling.

The method may further comprise a step of washing the red blood cells with at least one solvent (e.g., watery solvents, high concentration glycerol solvents) to remove undesired admixtures therefrom. The at least one solvent can be introduced into the flow chamber while the red blood cells are trapped within the acoustic standing wave. Prior to the washing step, the blood may be diluted, such as with saline (e.g., phosphate buffered saline). Alternatively, the blood may be undiluted whole blood and may be combined with the at least one solvent into a single flow that is flowed through the flow chamber at a flow rate of at least 4.5 mL/min.

In particular embodiments, a cryoprotectant may be added or removed from the blood.

The blood may further include platelets. In such embodiments, the ultrasonic transducer can be driven at varying frequencies to selectively isolate the red blood cells and platelets from the blood without causing hemolysis of the red blood cells or activation of the platelets.

In some embodiments, methods are provided for separating lipids from blood fluid. Blood fluid includes surgical blood, or blood that may be combined with components typically not found in blood, such as lipids, clots, bone fragments and other material that may result from surgery, injury or trauma. The methods may include flowing the blood fluid through a flow chamber of an acoustophoretic device, generating a multi-dimensional acoustic standing wave in the flow chamber to impose an acoustic radiation force on the blood fluid, such that the lipids in the blood fluid are retained and grouped to form larger groups of lipids in the acoustic standing wave against fluid drag force.

In particular embodiments, the multi-dimensional standing wave results in an acoustic radiation force having an axial force component and a lateral force component that are the same order of magnitude. In particular embodiments, the acoustic standing wave may be a multi-dimensional acoustic standing wave (e.g., a three-dimensional acoustic standing wave). Examples of such multi-dimensional acoustic standing waves can be found in commonly owned U.S. Pat. No. 9,228,183, the entire contents of which are hereby fully incorporated by reference. In other embodiments, the acoustic standing wave can be a planar acoustic standing wave. Further yet, in particular embodiments, the acoustic standing wave may be a combination of a planar acoustic standing wave and a multi-dimensional acoustic standing wave, such as where the planar acoustic standing wave and multidimensional acoustic standing wave are super-positioned on each other.

Some disclosed embodiments provide systems and/or methods for separating blood components and lipids from blood utilizing techniques that do not harm the blood component cells (e.g., erythrocytes, leukocytes, platelets) and that can be performed continuously, for example so blood can be recirculated during surgery. Some embodiments act to reduce the amount of lipids that are present in blood during surgery, so as to reduce microemboli and minor or major strokes in the patient.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 3A is a top view of a flow chamber and shows red blood cells (darker circles) and lipid particles (lighter circles) entering the system from the left-hand side and flowing horizontally therethrough. FIG. 3B is a top view of the flow chamber and shows the red blood cells and lipids becoming axially aligned in the acoustic standing wave. FIG. 3C is another top view of the flow chamber and shows the red blood cells and lipids agglomerating into clumps in well-defined striated columns due to the lateral force component of the acoustic standing wave. Finally, FIG. 3D is a cross-sectional side view of the flow chamber and shows that some of the red blood cells have agglomerated to a sufficient size and sunk to the bottom of the flow chamber, while the lipids have agglomerated to a sufficient size and risen to the top of the flow chamber.

FIG. 6A and FIG. 6B show the performance of the acoustophoretic device of FIG. 5. FIG. 6A is a chart that presents the red blood cell collection percentage of the device at different combinations of the feed flow rate ($\dot{V}_{in}$) and of the ratio of the flow rates of the filtrate outlet ($\dot{V}_f$) and the concentrate outlet ($\dot{V}_c$). FIG. 6B is a chart that presents the red blood cell concentration factor of the device at different combinations of the feed flow rate ($\dot{V}_{in}$) and of the ration of the flow rates of the filtrate outlet ($\dot{V}_f$) and the concentrate outlet ($\dot{V}_c$).

FIGS. 7A-7E are images that illustrate a lipid image analysis at 40× magnification. FIG. 7A shows lipid particles in saline immediately after spike. FIG. 7B shows the lipid particles in saline after filtration through a physical filter. FIG. 7C shows the lipid particles in saline after undergoing acoustic filtration according to the present disclosure. FIG. 7D shows the lipid particles in saline after agglomerating and rising to a lipid collection trap at the top of a flow chamber. FIG. 7E shows a top view of the lipid collection trap after filtration of the lipid particles according to the present disclosure.

FIG. 19 is a graph of electrical impedance amplitude versus frequency for a square transducer driven at different frequencies.

FIG. 20A is an illustration of the trapping line configurations for seven peak amplitudes of an ultrasonic transducer of the present disclosure. FIG. 20B is a perspective view illustrating a separator of the present disclosure. The fluid flow direction and the trapping lines are shown. FIG. 20C is a view from the fluid inlet along the fluid flow direction (arrow 814) of FIG. 20B, showing the trapping nodes of the standing wave where particles would be captured. FIG. 20D is a view taken through the transducers face at the trapping line configurations, along arrow 816 as shown in FIG. 20B.

DETAILED DESCRIPTION

Figure 1A:
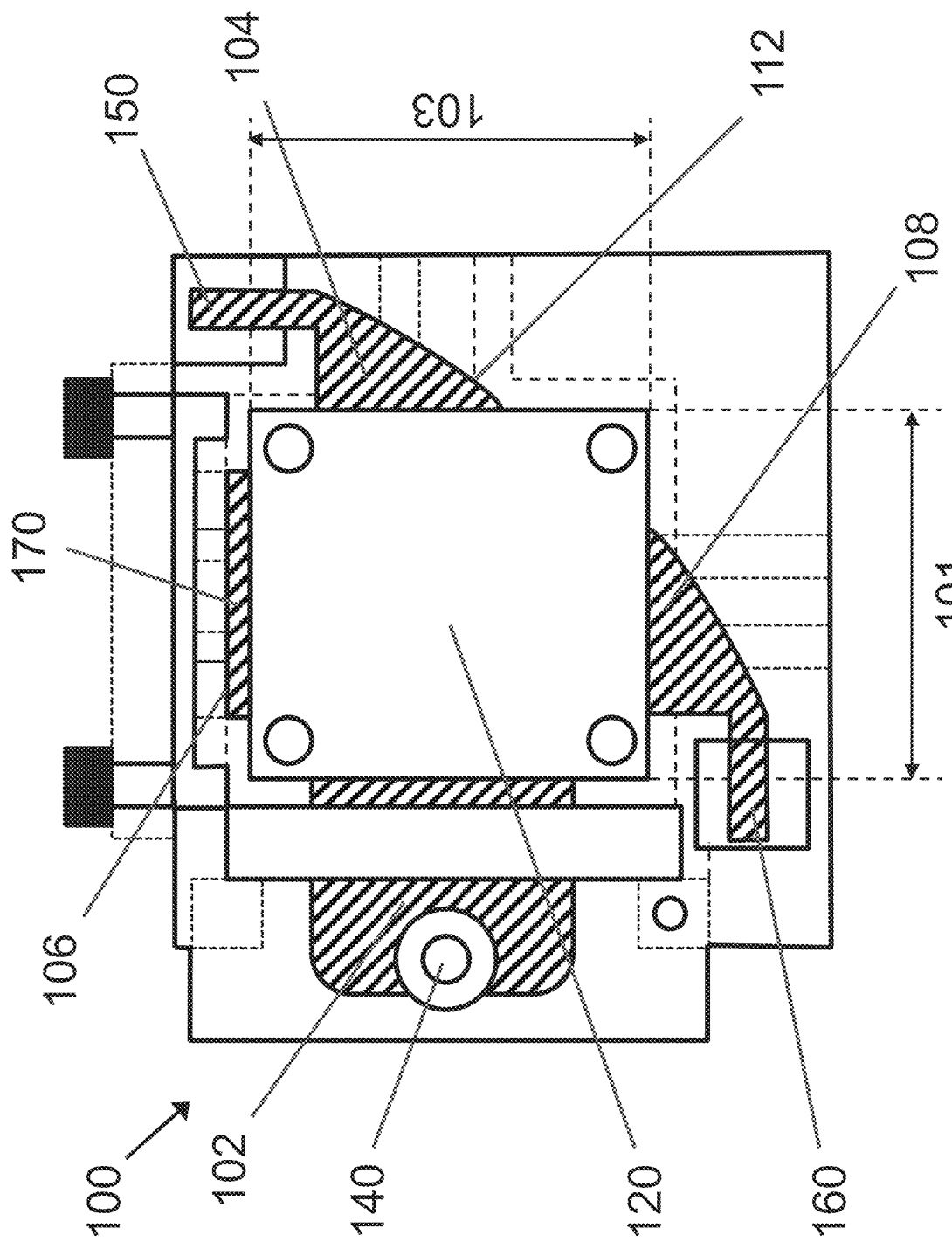
FIG. 1A is an exterior side view of a first exemplary embodiment of an acoustophoretic device according to the present disclosure.

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

The term "comprising" is used herein as an open-ended word that includes the presence of the named component and allows the presence of other components. The term "comprising" should be construed to include the term "consisting of", which allows the presence of only the named component, along with any impurities that might result from the manufacture of the named component.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

The modifier "about" used in connection with a quantity is inclusive of the stated value and has the meaning dictated by the context. When used in the context of a range, the modifier "about" should also be considered as disclosing the range defined by the absolute values of the two endpoints. For example, the range of "from about 2 to about 10" also discloses the range "from 2 to 10." The term "about" may refer to plus or minus 10% of the indicated number. For example, "about 10%" may indicate a range of 9% to 11%, and "about 1" may mean from 0.9-1.1.

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "top" and "bottom" or "base" are used to refer to surfaces where the top is always higher than the bottom/base relative to an absolute reference, i.e. the surface of the earth. The terms "upwards" and "downwards" are also relative to an absolute reference; upwards is always against the gravity of the earth.

The term "parallel" should be construed in its lay sense of two surfaces that maintain a generally constant distance between them, and not in the strict mathematical sense that such surfaces will never intersect when extended to infinity.

The present application refers to "the same order of magnitude." Two numbers are of the same order of magnitude if the quotient of the larger number divided by the smaller number is a value of at least 1 and less than 10.

As previously mentioned, efficient separation technologies for multi-component liquid streams, such as red blood cells and/or lipids from blood, are desirable. In this regard, as used herein, the term "blood" refers to the combination of blood cells suspended in plasma. As used herein, the term "plasma" refers to the liquid component of blood that contains dissolved proteins, glucose, clotting factors, mineral ions, hormones and carbon dioxide. As used herein, the term "blood cells" refers to both red blood cells and white blood cells.

The term "crystal" refers to a single crystal or polycrystalline material that is used as a piezoelectric material.

The present disclosure relates to systems and methods for separating RBCs and lipid contaminants from blood using multi-dimensional acoustic standing waves (ASWs). These systems and methods also provide the potential to perform washing of blood cells, which makes them particularly desirable for the healthcare market. The systems and methods according to the present disclosure combine ASW-based inherent advantages, such as efficient separation, low power consumption, controllability, and gentle cell handling, with the sufficiently high throughput demanded by many clinical and healthcare applications. Moreover, the filtration efficiency for lipid separation using these ASW-based systems can be better than that of conventional methods, such as filter screens and centrifugation, because agglomeration and coalescence of smaller particles in the present ASW-based systems and methods permit capture and removal of lipid particles too small for filters and centrifuges.

The feasibility of the present approach has been demonstrated on the micro-scale in MEMS work by using acoustophoresis to sort lipid and blood cells into different outlets. Such a micro-scale approach may not meet the volume and flow rates demanded for real world application. In the present disclosure, a macro-scale acoustophoresis device is described that is able to achieve flow rates of up to 2 liters/hour, which is at or above the optimal clinical reinfusion rate.

Modern hemotherapy practice has evolved to the targeted use of separate blood elements (i.e. component therapy, CT), such as red bloods cells (RBCs), platelets, or plasma. Several studies recently have raised concerns regarding the development of 'storage lesions' affecting CT packed RBCs, which affect the transfusion recipient treated with them. For example, RBCs accumulate structural and biochemical damage due to ex vivo storage at 4° C. Adverse effects from this damage can be managed by cell washing procedures that remove ineffective RBCs and metabolic degradation products and markedly improve the quality of the product to be transfused. A similar treatment can also potentially restore usability of an RBC concentrate that is weeks past its shelf life. While the typical storage period of packed RBCs is limited per regulatory guidelines to only several weeks in common practice, when the products are preserved in liquid state at 4° C., the storage period can be extended up to at least 10 years (and possibly for several decades) by cryopreservation.

In emergency situations, such as natural disasters, wars, and acts of terror, transfusions of blood products may be urgently life-saving, but due to logistical and transportation issues, routinely stocked clinical blood banks may be incapable of meeting the increased demands quickly and effectively. In such situations, the use of cryopreserved stocks, as well as potentially the use of expired blood restored by washing procedures, may help to stabilize patients during the critical first hours of care. High numbers of patients with massive trauma is another hallmark of such emergencies. In this case, collecting the patient's own blood and removing contaminants to make it usable for auto-transfusion may be the best available hemotherapy, allowing early treatment and surgical interventions where indicated. The amount of blood to be processed in this case is unpredictable and, therefore, a system capable of processing variable volumes is desirable. Finally, force majeure situations may impose challenges in performing patient care under adverse and inhospitable field conditions devoid of electrical power or means to transport heavy equipment to the point of care.

Blood processing systems typically used in clinical practice are large, heavy, and power-hungry devices that are operated by trained personnel. Therefore, these systems are largely restrained to clinical use, and their application in field conditions is hardly practical. Available systems are highly specialized. The systems used to process blood collected from surgical fields prior to reinfusion (such as Cell Saver 5+, Haemonetics, MA) differ from those used in blood banking for washing and cryoprotectant management (such as ACP 215, Haemonetics, or CaBE 2991, Terumo, Shibuya, Japan). These are stationary, hospital ward-bound systems, which are large ($0.55 \times 0.43 \times 0.31$ m$^3$ for ACP 215 or $0.94 \times 0.41 \times 0.37$ m$^3$ for Cell Saver), heavy (25 kg or 32 kg), and use high power for their operation (500 W or 300 W). These systems typically use centrifugation to separate blood components, which results in the large size and complexity of these conventional systems.

In contrast to those systems, the systems and devices of the present disclosure utilize multi-dimensional acoustic standing waves (ASWs). An important feature of ASW-based systems is their small size and low power consumption, which aids in portability. They are also amenable to automation and to easy maintenance, primarily because they do not include rotors driven at high speed. The multi-dimensional (e.g., three-dimensional) ASW technology of the present disclosure permits a portable ASW system to be used for blood treatment.

The systems and devices of the present disclosure do not have the same limitations as prior large, heavy, and power-hungry devices. Portability of the systems and devices is enhanced by the absence of a centrifuge. Universality is another important feature that favors the systems and device of the present disclosure for emergencies. The systems and devices of the present disclosure can be used to de-glycerolize RBC concentrates from deep-frozen stocks and make them available in urgent transfusions to stabilize patients. Additionally, the systems and devices can be used for purification and re-transfusion of blood loss caused by trauma. One more important feature is that an ASW-based process is essentially continuous and is not limited by batch size, in contrast to present systems. Therefore, the systems and devices of the present disclosure can be used for blood treatment when the total volume of blood is not known a priori, which is important in trauma surgery. The combination of multiple uses in a single device and high levels of automation will save valuable time for healthcare personnel, especially in emergency situations.

Simplification of the blood processing for cryopreservation and thawing of blood units will positively augment blood resources, potentially decreasing the overall demand for allogeneic blood collections to meet the increasing demands in a clinically aging population. The ability to build cryopreserved stocks of rare blood types will also be enhanced. Because the systems and devices disclosed herein are capable of removing lipid particles, which are the cause of microemboli, with better efficiency than the current systems and because they can process any volume of blood, the systems and devices disclosed herein provide a better choice for general trauma, orthopedic, and cardiac surgery. In other words, these systems and devices will both help to boost efficiency in clinical practice and to improve patient well-being.

There exist additional developmental potentials for the systems and methods disclosed herein that are not available with current centrifugal systems. For example, the selectivity of the acoustic standing wave(s) used herein can be modified by changing the operation frequency. The higher the frequency, the smaller the wavelength and, hence, smaller particles can be trapped. This effect may be employed for fractionation of cells by size, such as separation of platelets from RBCs and WBCs. In addition, because there are no known adverse effects on live cells due to acoustic trapping, blood can be recirculated through the system for multiple process cycles. This can enhance performance of the operations that are insufficiently selective with a single cycle. On the other hand, the ability to use multiple cycles to perform an operation may reduce the system size and the dead volume. Next, acoustics control is independent from flow control; therefore, separation by ASW technology can be augmented by combining it with fluidics manipulation. The flexibility and power of such an approach have been widely demonstrated in the MEMS domain. There is an expectation that washing of RBCs in an ASW system will be more efficient due to the lack of cell compression, which is inherent in centrifugal applications. Isolation of platelets and leukapheresis is also contemplated. The ability to isolate and fractionate the "buffy coat" is a first step in selecting T-cells from a cancer patient blood or stem cells from umbilical cord blood. Both immune and stem cells are at the core of the rapidly growing cell therapy manufacturing.

The acoustophoretic systems, devices, and methods of the present disclosure advantageously provide the ability to capture, separate, and cause particles to separate out of an active fluid flow. As such, these systems, devices, and methods can replace traditional physical filtration, sedimentation, or centrifugation techniques.

Acoustophoresis

Acoustophoresis, as applied in the present disclosure, is a low-power, no-pressure-drop, no-clog, solid-state approach for the separation of particles, secondary fluids, and/or components (e.g., red blood cells (RBCs), white blood cells (leukocytes), platelets, lipids) from a primary or host fluid (e.g., blood) using high-intensity acoustic standing waves, and without the use of membranes or physical size exclusion filters. It has been known that high intensity standing waves of sound can exert forces on particles in a fluid when there is a differential in both density and/or compressibility, otherwise known as the acoustic contrast factor. The pressure profile in a standing wave contains areas of local minimum pressure amplitudes at its nodes and local maxima at its anti-nodes. Depending on the density and compressibility of the particles, they will be trapped at the nodes or anti-nodes of the standing wave. Generally, the higher the frequency of the standing wave, the smaller the particles that can be trapped due the pressure of the standing wave.

Acoustophoresis can be used to separate similarly sized blood cells and lipids from each other, so that either the blood cells, the lipids, or both can be collected. Acoustophoresis can be used in a continuous flow process, in which the blood flows through a flow chamber, allowing a continuous loop process without any flow interruption. In this way, the devices of the present disclosure can be autonomous and continuously operated, which can be particularly advantageous for certain applications, and allows for use of the devices without the need for any specially trained personnel. In the flow chamber, the blood cells and lipids are separated from the plasma, and can thus be removed from the blood/plasma. This can be useful for example during surgery, when lipids are introduced into the bloodstream of a surgery patient. The lipids can be removed from the bloodstream during the external circulation loop of the blood, reducing the likelihood of lipid micro-emboli due to the surgery. The removal of lipids can reduce post-surgery complications.

Figure 1B:
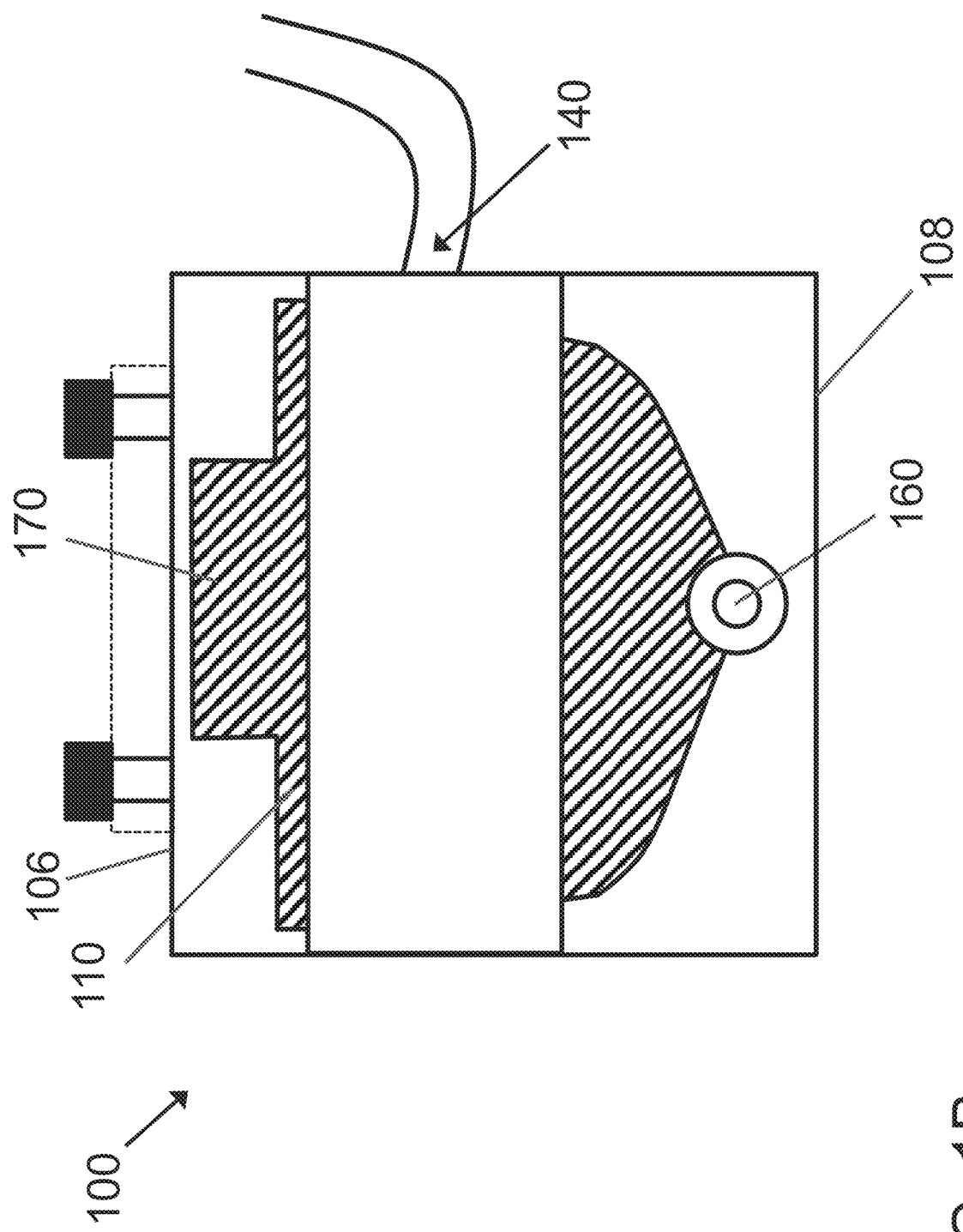
FIG. 1B is an exterior view of the first embodiment from the front.
Figure 1C:
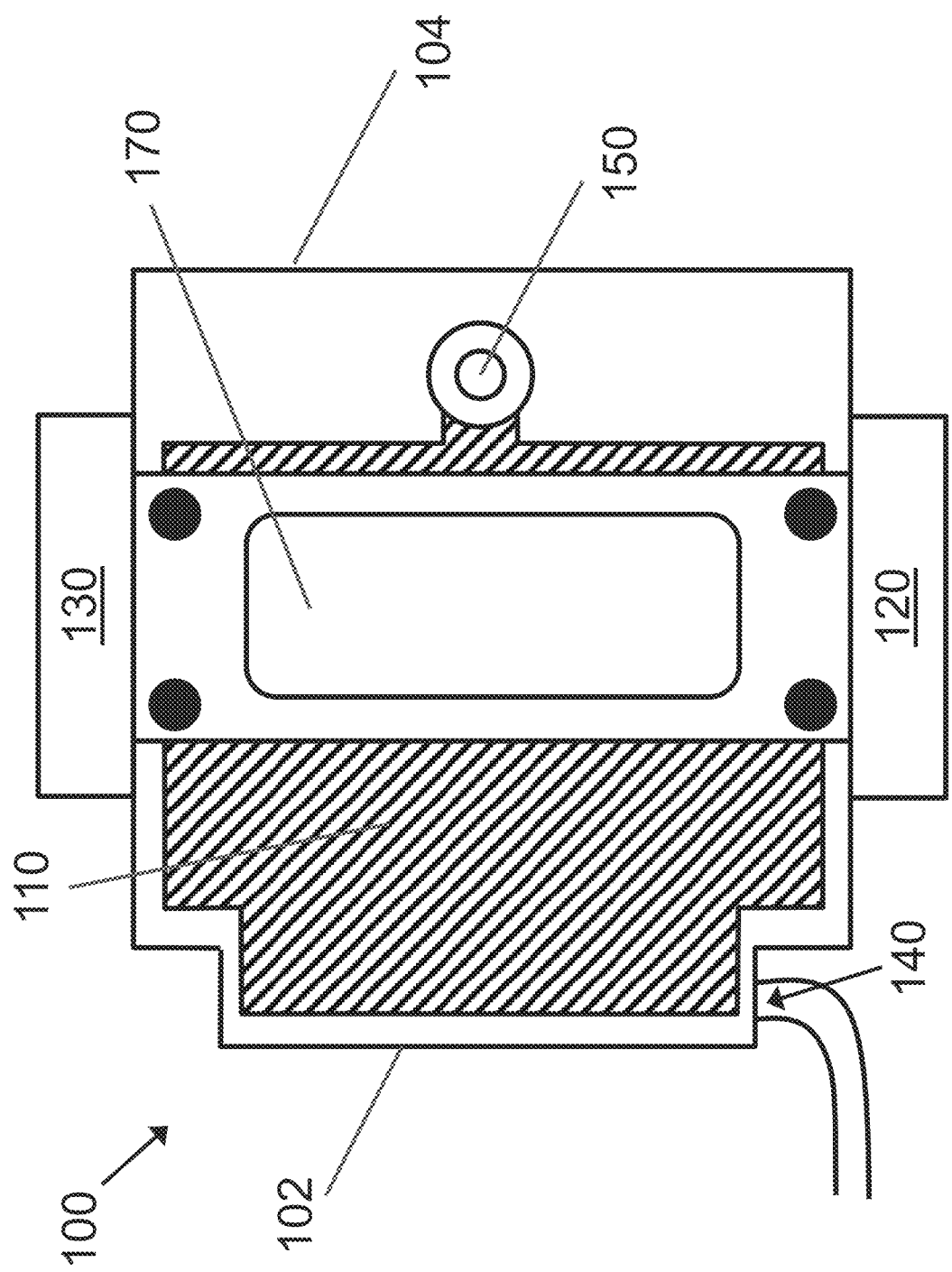
FIG. 1C is an exterior view of the first embodiment from the top.
Figure 2:
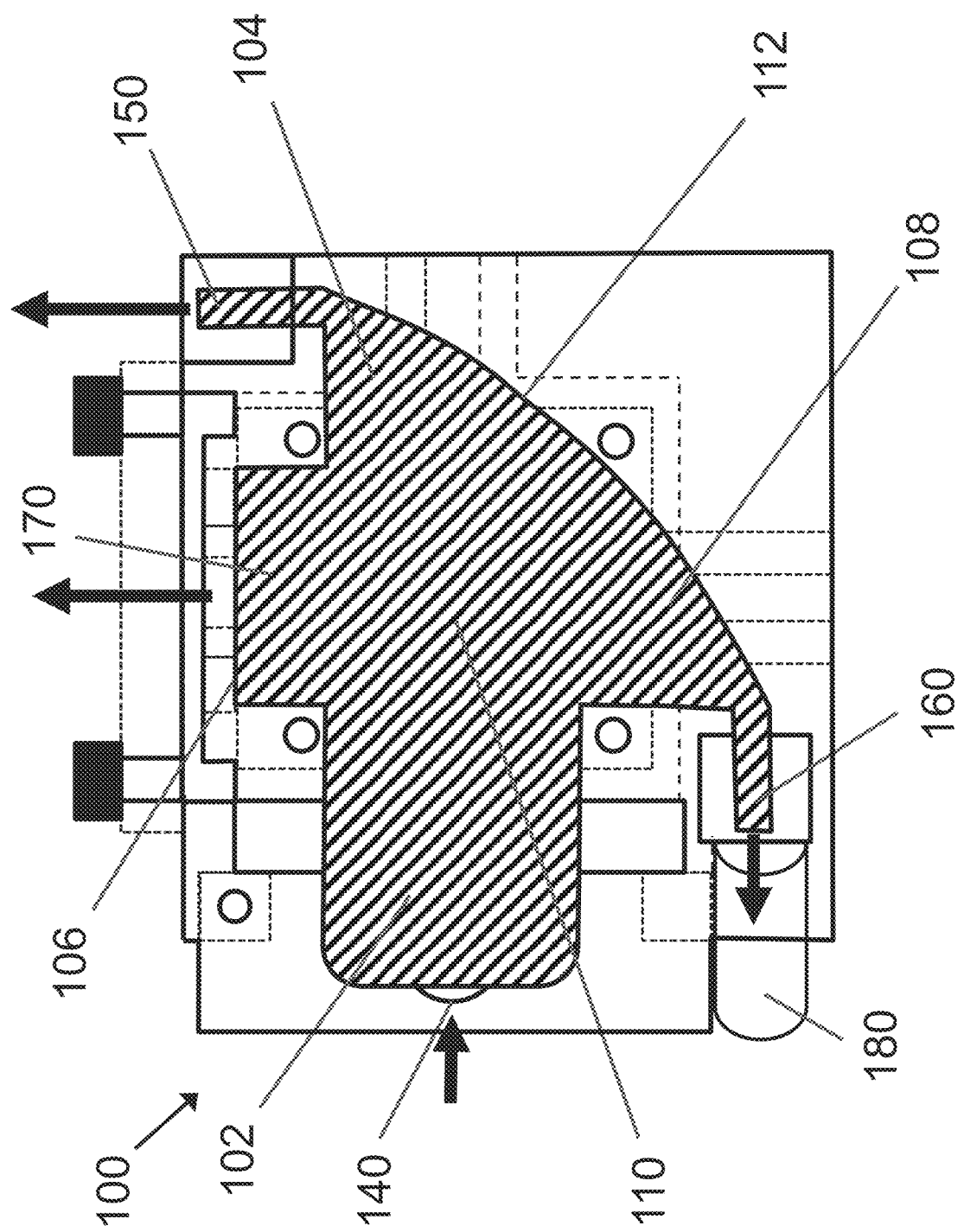
FIG. 2 is an interior sidecross-sectional view that illustrates additional features of the acoustophoretic device of FIG. 1A.

With reference now to FIGS. 1A-1C and FIG. 2, a first exemplary embodiment of an acoustophoretic device 100 for separating blood components (e.g., lipids, blood cells) from blood is depicted. FIG. 1A is an external side view, FIG. 1B is an external front view, and FIG. 1C is an external top view, while FIG. 2 is an interior view.

The device 100 includes a flow chamber 110, which can be best seen in FIG. 2. The flow chamber 110 is the region of the device 100 through which blood containing blood components flows. In the embodiment shown in FIG. 1C and FIG. 2, the device 100 includes an inlet 140 on a first side 102 of the flow chamber 110. The flow chamber 110 further includes at least two outlets. First, a filtrate outlet 150 is present. In the embodiment shown in FIG. 1A and FIG. 2, the filtrate outlet 150 is located on a second side 104 of the flow chamber 110. As can be seen in FIG. 1C and FIG. 2, the second side 104 of the flow chamber 110 is located opposite the first side 102 thereof, such that, in this embodiment, the inlet 140 is located on an opposite side of the flow chamber 110 from the filtrate outlet 150. A concentrate outlet 160 is also present in the flow chamber 110. The concentrate outlet 160 is located at a bottom end 108 of the flow chamber 110. In the embodiment shown in FIG. 1A and FIG. 2, the flow chamber 110 also includes a lipid collection trap 170 at a top end 106 thereof. As can be seen in FIG. 1B and FIG. 2, the top end 106 of the flow chamber 110 is located opposite the bottom end 108 thereof, such that, in this embodiment, the lipid collection trap 170 is located on an opposite end of the flow chamber 110 from the concentrate outlet 160. In particular embodiments, the flow chamber 110 can have an interior volume of at least 50 mL, such that the device 100 remains lightweight and portable.

As can be best seen in FIG. 1A and FIG. 1B, the flow chamber includes an ultrasonic transducer 120 positioned on a wall thereof. On an opposite wall (i.e., on the opposite side of the flow chamber), a reflector 130 is positioned so as to set up a multi-dimensional acoustic standing wave in the flow chamber, as described in detail herein. The transducer 120 has a width 101 and a height 103. Very generally, the ultrasonic transducer-reflector pair generates the multi-dimensional acoustic standing wave in the flow chamber therebetween. Put another way, the acoustic standing wave is generated in the flow chamber between the ultrasonic transducer and the reflector and generally does not extend beyond those respective surfaces. In this way, as can be seen in FIG. 1A and FIG. 2, when the lipid collection trap 170 is provided, it is located within the flow chamber 110 at the top end 106 thereof above the acoustic standing wave. Similarly, in the embodiment shown in FIG. 1C and FIG. 2, the filtrate outlet 150 is located on a second side 104 of the flow chamber 110 outside of the acoustic standing wave. Finally, as can be seen in FIG. 1B and FIG. 2, the concentrate outlet 160 is located within the flow chamber 110 at the bottom end 108 thereof below the acoustic standing wave.

As can be best seen in FIG. 2, the flow chamber 110 includes an angled wall 112 that tapers from the filtrate outlet 150 to the concentrate outlet 160. In particular, the shallow wall 112 tapers from the second side 104 of the flow chamber 110 towards the bottom end 108 thereof, or put another way is opposite the inlet. In this way, at higher flow rates through the device 100, the shallow wall 112 can aid in deflecting the filtrate (i.e., clarified blood) upward towards the filtrate outlet 150 and agglomerated particles denser than the blood (e.g., blood cells) downward towards the concentrate outlet 160. The shallow wall 112 further prevents any undesirable build-up or clogging of the flow chamber and minimizes the dead volume because the device contains shorter connection lines than a comparable centrifuge system, whose size is restricted by the rotor geometry. The devices and systems of the present disclosure therefore have a much higher potential to eliminate fat and lipid contamination, decreasing the embolism risks of peri-operatively collected autologous blood from the surgical field for hemotherapy.

In particular applications in which the separation and/or removal of lipids from the blood is not critical, it is contemplated that the filtrate outlet 150 could be located at the top end 106 of the flow chamber 110 (e.g., in the location of the lipid collection trap 170 currently depicted in FIG. 1A and FIG. 2). That is, the filtrate outlet 150 can be located in the flow chamber 110 at the top end 106 thereof above the acoustic standing wave. Put another way, no lipid collection trap is present in such embodiments.

In certain embodiments, such as in the embodiment depicted in FIG. 2, the device 100 can also include a container 180 (e.g., a bag) that is detachably connected to the concentrate outlet 160. The container 180 is configured to automatically seal upon detachment from the concentrate outlet 160 without comprising the sterility of any material held within the container 160. Such self-sealing containers are known in the art. The container 160 is usable for transfusions at body temperature and for low-temperature storage as low as −80° C. As also illustrated here, blood enters through inlet 140. Clarified blood exits through filtrate outlet 150, and concentrate exits through the concentrate outlet 160. If desired, lipids can also be removed through lipid collection trap 170. These flows are indicated with arrows.

Figure 3:
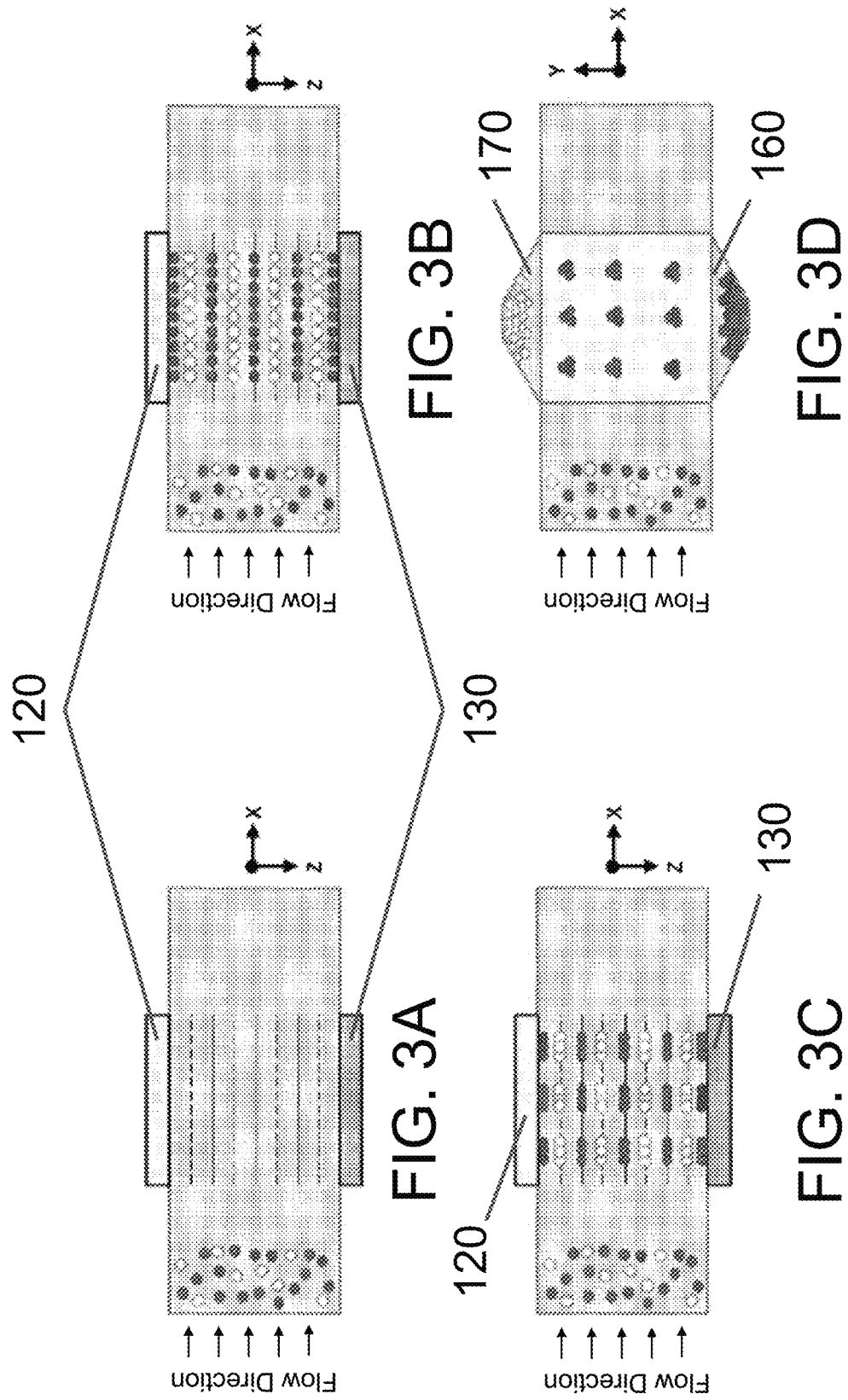
FIGS. 3A-3D are diagrams illustrating acoustophoretic separation methods according to the present disclosure.

The flow chamber operates as shown in FIGS. 3A-3D. As shown in FIG. 3A, the transducer 120 and reflector 130 generate an acoustic standing wave that establishes pressure nodes (solid lines) and anti-nodes (dashed lines) in the acoustic standing wave between the transducer and reflector pair. As can be seen in FIG. 3B, the axial force component of the acoustic radiation force generated by the acoustic standing wave aligns the red blood cells and lipids in the nodal/antinodal lines based on acoustic contrast factor. FIG. 3C shows how the lateral force component of the acoustic radiation force generated by the acoustic standing wave causes agglomeration/coalescence of the red blood cells and lipids into clumps within the planes to create striated columns of aggregated materials. FIG. 3D is a cross-sectional side view of a nodal plane and shows that as the agglomerated clumps increase in size, they either rise or sink out of the acoustic standing wave due to enhanced buoyancy or gravitational settling, respectively. For example, the red blood cells, which are more dense than the plasma, agglomerate and then fall into the concentrate outlet 160 at the bottom of the flow chamber due to enhanced gravitational settling, while the lipids, which are less dense than plasma, agglomerate and rise to the lipid collection trap 170 at the top of the flow chamber due to enhanced buoyancy.

Put another way, as will be explained in greater detail below, materials denser than plasma (e.g., blood cells) that are trapped within the acoustic standing wave will agglomerate or coalesce within the acoustic standing wave before growing to a sufficient size that they fall out of the acoustic standing wave due to enhanced gravitational settling and fall to the concentrate outlet 160 below the acoustic standing wave. Similarly, materials less dense than plasma (e.g., lipids) that are trapped within the acoustic standing wave will agglomerate or coalesce within the acoustic standing wave before growing to a sufficient size that they rise out of the acoustic standing wave due to enhanced buoyancy and rise to the lipid collection trap 170 above the acoustic standing wave. The filtrate (i.e., clarified blood) flows from the inlet 140 to the filtrate outlet 150 after being clarified of components by the acoustic standing wave.

The acoustophoretic device is designed to create a high intensity multi-dimensional (e.g., three-dimensional) acoustic standing wave that results in an acoustic radiation force that is larger than the combined effects of fluid drag and buoyancy, and is therefore able to trap, i.e., hold stationary, the suspended phase (e.g., particles or a secondary fluid). This effective result is an important distinction from previous approaches where particle trajectories were merely altered by the effect of the acoustic radiation force without any trapping of the particles. The present systems and devices have the ability to create ultrasonic standing wave fields that can trap particles in flow fields with linear velocity of about 10 mL/min to about 60 Ml/min, and even higher. Excellent particle separation efficiencies have been demonstrated for particle sizes as small as one micron. As can be seen in Table 1 below, such particle sizes are much smaller than blood and lipid cells.

TABLE 1

Relevant Properties of Particles

| Particle | RBC | Lipid |
| --- | --- | --- |
| Diameter (µm) | 6 | 10-60 |
| Density (kg/m$^3$) | 1092 | 921 |
| Compressibility (Pa$^{-1}$) | 3.5E-10 | 5.2E-10 |
| Acoustic Contrast Factor | 0.32 | −0.22 |

Generally, the scattering of the acoustic field off the particles results in a three-dimensional acoustic radiation force, which acts as a three-dimensional trapping field. The acoustic radiation force is proportional to the particle volume (e.g., the cube of the radius) when the particle is small relative to the wavelength. It is proportional to frequency and the acoustic contrast factor. It also scales with acoustic energy (e.g. the square of the acoustic pressure amplitude). For harmonic excitation, the sinusoidal spatial variation of the force is what drives the particles to the stable positions within the standing waves. When the acoustic radiation force exerted on the particles is stronger than the combined effect of fluid drag force and buoyancy/gravitational force, the particle is trapped within the acoustic standing wave field. The action of the acoustic forces (i.e., lateral and axial acoustic forces) on the trapped particles results in formation of tightly packed clusters through concentration, agglomeration and/or coalescence of particles that settle through enhanced gravity (particles heavier than the host fluid) or buoyancy (particles lighter than the host fluid). Additionally, secondary inter-particle forces, such as Bjerkness forces, aid in particle agglomeration.

Most biological cell types present a higher density and lower compressibility than the medium in which they are suspended, so that the acoustic contrast factor between the cells and the medium has a positive value. As a result, the axial acoustic radiation force (ARF) drives the cells towards the standing wave pressure nodes. The axial component of the acoustic radiation force drives the cells, with a positive contrast factor, to the pressure nodal planes, whereas cells or other particles with a negative contrast factor are driven to the pressure anti-nodal planes. The radial or lateral component of the acoustic radiation force is the force that traps the cells. The radial or lateral component of the ARF is larger than the combined effect of fluid drag force and gravitational force. For small cells or emulsions the drag force $F_D$ can be expressed as:

$$\vec{F}_D = 4\pi \mu_f R_p (\vec{U}_f - \vec{U}_p) \left[ \frac{1 + \frac{3}{2}\hat{\mu}}{1 + \hat{\mu}} \right]$$

where $U_f$ and $U_p$ are the fluid and cell velocity, $R_p$ is the particle radius, $\mu_f$ and $\mu_p$ are the dynamic viscosity of the fluid and the cells, and $\hat{\mu}=\mu_p/\mu_f$ is the ratio of dynamic viscosities. The buoyancy force $F_B$ is expressed as:

$$F_B = \frac{4}{3}\pi R_p^3 (\rho_f - \rho_p)$$

For a cell to be trapped in the multi-dimensional ultrasonic standing wave, the force balance on the cell can be assumed to be zero, and therefore an expression for lateral acoustic radiation force $F_{LRF}$ can be found, which is given by:

$$F_{LRF} = F_D + F_B.$$

For a cell of known size and material property, and for a given flow rate, this equation can be used to estimate the magnitude of the lateral acoustic radiation force.

One theoretical model that is used to calculate the acoustic radiation force is based on the formulation developed by Gor'kov. The primary acoustic radiation force $F_A$ is defined as a function of a field potential U, $F_A = -\nabla(U)$, where the field potential U is defined as $$U = V_0 \left[ \frac{\langle p^2 \rangle}{2\rho_f c_f^2} f_1 - \frac{3\rho_f \langle u^2 \rangle}{4} f_2 \right],$$

and $f_1$ and $f_2$ are the monopole and dipole contributions defined by $$f_1 = 1 - \frac{1}{\Lambda \sigma^2}, \qquad f_2 = \frac{2(\Lambda - 1)}{2\Lambda + 1},$$

where p is the acoustic pressure, u is the fluid particle velocity, $\Lambda$ is the ratio of cell density $\rho_p$ to fluid density $\rho_f$, $\sigma$ is the ratio of cell sound speed $c_p$ to fluid sound speed $c_f$, $V_o$ is the volume of the cell, and < > indicates time averaging over the period of the wave.

Gork'ov's model is for a single particle in a standing wave and is limited to particle sizes that are small with respect to the wavelength of the sound fields in the fluid and the particle. It also does not take into account the effect of viscosity of the fluid and the particle on the radiation force. As a result, this model cannot be used for the macro-scale ultrasonic separators discussed herein since particle clusters can grow quite large. A more complex and complete model for acoustic radiation forces that is not limited by particle size was therefore used. The models that were implemented are based on the theoretical work of Yurii Ilinskii and Evgenia Zabolotskaya as described in AIP Conference Proceedings, Vol. 1474-1, pp. 255-258 (2012). These models also include the effect of fluid and particle viscosity, and therefore are a more accurate calculation of the acoustic radiation force.

The lateral force of the total acoustic radiation force (ARF) generated by the ultrasonic transducers of the present disclosure is significant and is sufficient to overcome the fluid drag force. Additionally, as explained above, this action of the acoustic forces (i.e., lateral and axial acoustic forces) on the trapped particles results in formation of tightly packed clusters through concentration, agglomeration and/ or coalescence of particles that settle through enhanced gravity (particles heavier than the host fluid) or buoyancy (particles lighter than the host fluid). Relatively large solids of one material can thus be separated from smaller particles of a different material, the same material, and/or the host fluid through enhanced gravitational separation.

The multi-dimensional standing wave generates acoustic radiation forces in both the axial direction (i.e., in the direction of the standing wave, between the transducer and the reflector, perpendicular to the flow direction) and the lateral direction (i.e., in the flow direction). As the mixture flows through the flow chamber, particles in suspension experience a strong axial force component in the direction of the standing wave. Since this acoustic force is perpendicular to the flow direction and the drag force, it quickly moves the particles to pressure nodal planes or anti-nodal planes, depending on the contrast factor of the particle. The lateral acoustic radiation force then acts to move the concentrated particles towards the center of each planar node, resulting in agglomeration or clumping. The lateral acoustic radiation force component overcomes fluid drag, which permits clumps of particles to continually grow and then drop out of the mixture due to gravity. A drop in drag per particle as the particle cluster increases in size and a drop in acoustic radiation force per particle as the particle cluster grows in size may be considered together or independently in the operation of the acoustic separator device. In at least some examples in the present disclosure, the lateral force component and the axial force component of the multi-dimensional acoustic standing wave are of the same order of magnitude. In this regard, it is noted that in a multi-dimensional acoustic standing wave, the axial force may have a different value than the lateral force, e.g. be weaker or stronger, or may be equal or equivalent, but the lateral force of a multi-dimensional acoustic standing wave is greater than the lateral force of a planar standing wave, sometimes by two orders of magnitude or more.

Testing to Measure RBC Separation Efficiency and Concentration Factor

Figure 4:
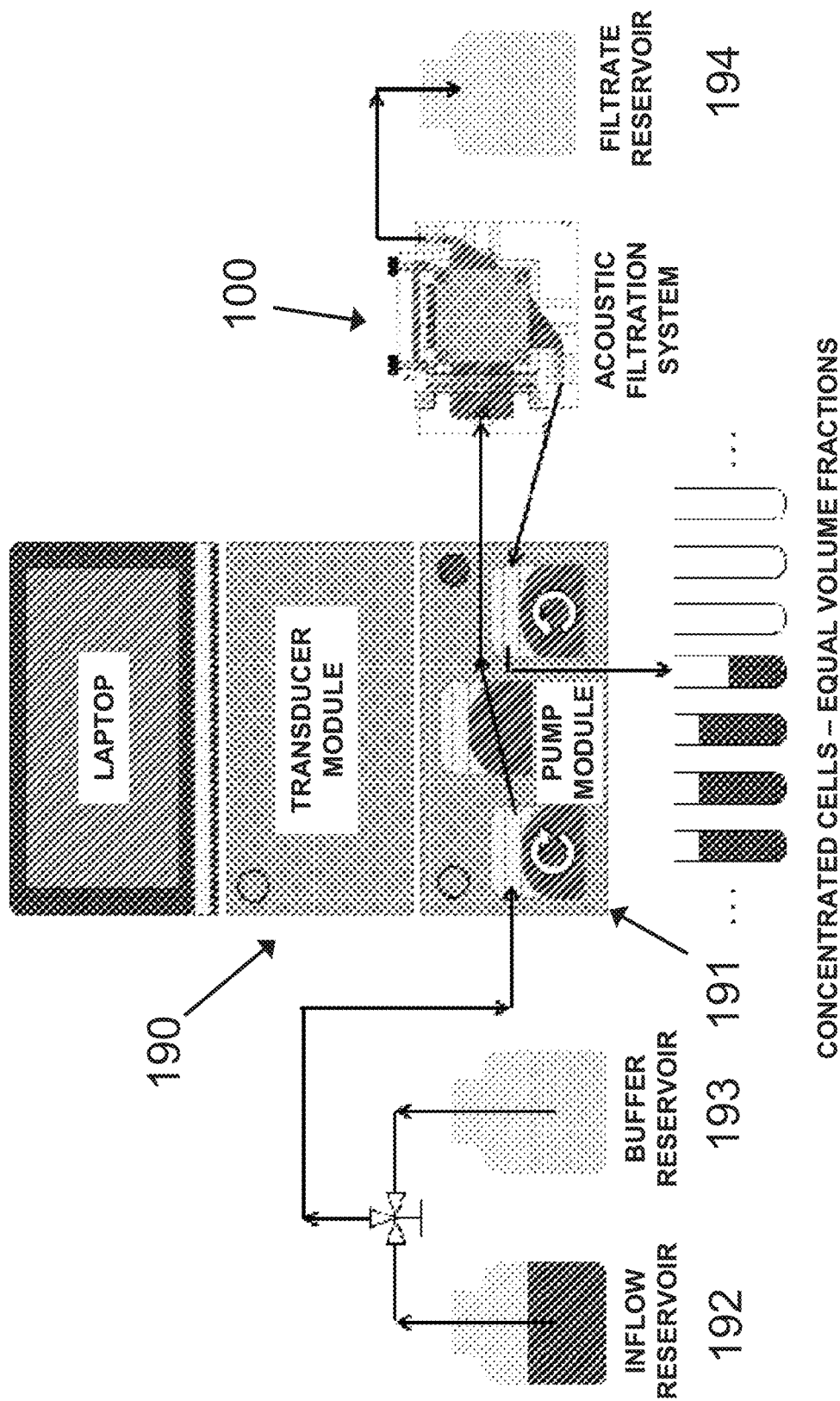
FIG. 4 is a diagram that illustrates a system for testing/operating an acoustophoretic device according to the present disclosure. The components includes a laptop, a transducer control module, a pump module, an inflow reservoir, a buffer reservoir, an acoustic filtration system (e.g., an acoustophoretic device according to the present disclosure), and a filtrate reservoir.

Turning now to FIG. 4, a schematic illustration of a system that uses the acoustophoretic device is shown. This system was also used to test the performance of the acoustophoretic device. A transducer module 190 controlled the mechanical output of a transducer used in an acoustic filtration device 100 to create a multi-dimensional acoustic standing wave at high frequencies (1-3 MHz) and high amplitude (up to 100 V). The resonator section of the acoustic filtration device (i.e., defined by the transducer-reflector pair in which the acoustic standing wave is generated) can detune because of accumulation of material (e.g., blood cells, lipids) and change of temperature during the operation. To restore the optimal operation, the transducer control module 190 periodically scans the adjacent frequency region and switches for the optimal frequency under the current conditions. Peristaltic pumps of the pump module 191 are used to independently control the flows of the feed from the inflow reservoir 192 and the buffer reservoir 193 (i.e., at the inlet) and RBC collection (i.e., at the concentrate outlet). The output from the filtrate outlet of the acoustic device 100 is collected in filtrate reservoir 194. A fraction collector was used to collect the eluted material during the operation at known times and characterize the acoustic system performance at different stages of the operation. The tests were performed with porcine blood purchased from Hemostat Laboratories, CA.

Optimization of the protocols of the designed system included identification of the transducer power range, the fluid flows through the system, and tests of the performance of the system at different dilutions of the blood sample. When the power is too low, the acoustic forces are too weak to trap the particles and to hold them against the flow. However, when the power is too high, the acoustic force interferes with the gravitational precipitation and the transducer may heat the resonator to temperatures too high for live cell treatment. During testing, it was found that a driving amplitude of 22.5 V provided sufficient retention, while the temperature rise throughout the resonator was at most 2° C. (on the transducer surface). Because all experiments were performed at room temperature, this heating was not dangerous.

Figure 5:
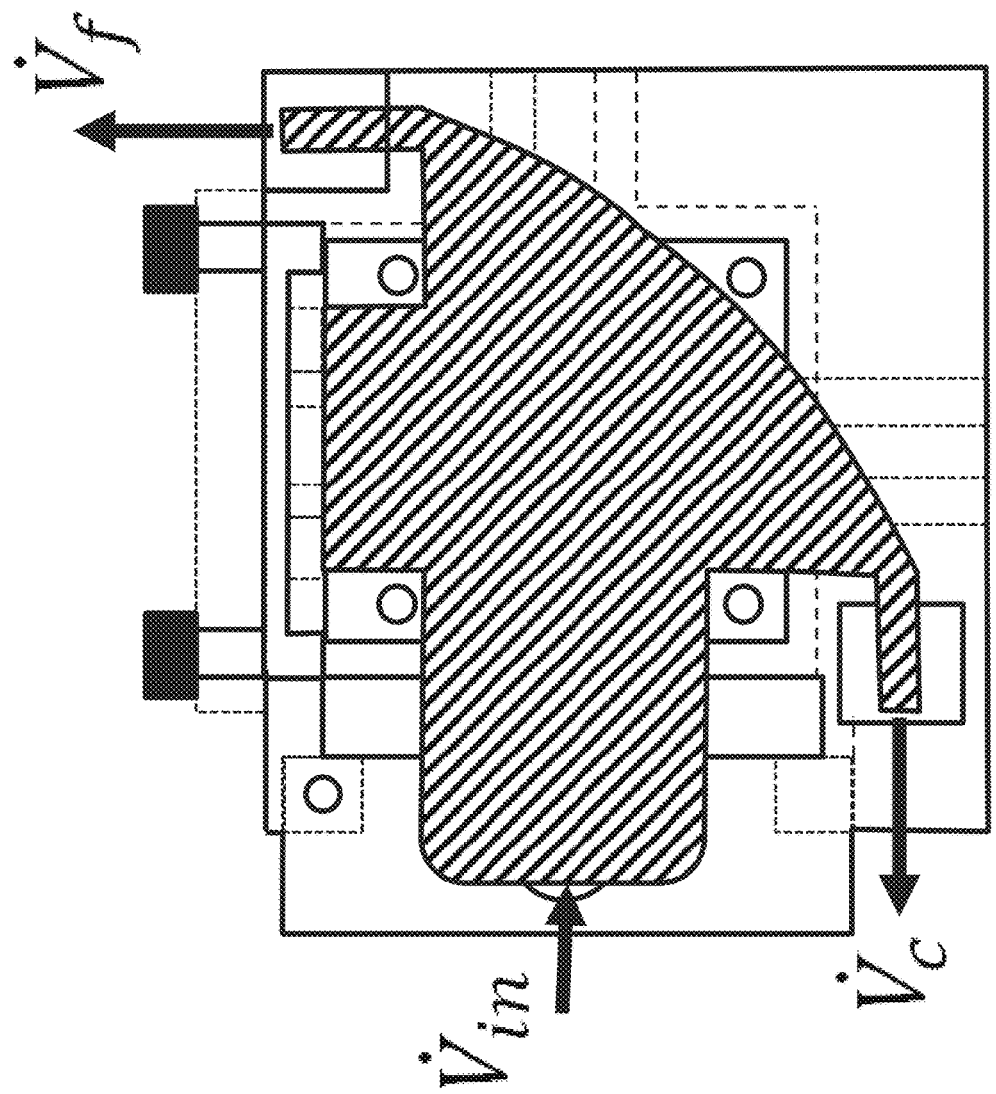
FIG. 5 is an interior side cross-sectional view that illustrates the fluid flow path through the acoustophoretic device of FIG. 1. Fluid (e.g., blood) enters the device at the inlet thereof with a flow rate $\dot{V}_{in}$ and continues into the flow chamber and through the acoustic standing wave. The filtrate (i.e., clarified fluid) exits the device at a flow rate $\dot{V}_f$. The concentrated cells (e.g., red blood cells) exit the device at a flow rate $\dot{V}_c$.

FIG. 5 illustrates the fluid flow path through the acoustic filtration system (e.g., the acoustophoretic device of FIG. 1). Blood entered the device at the inlet thereof with a flow rate $\dot{V}_{in}$ and continued into the flow chamber and through the acoustic standing wave. The filtrate (i.e., clarified fluid) exits the device at a flow rate $\dot{V}_f$. The concentrated cells (e.g., red blood cells from blood) exit the device at a flow rate $\dot{V}_c$. To determine the optimal combination of inflows and outflows, the system performance was characterized over a wide range of flow rates. The data matrices presented in FIG. 6A and FIG. 6B show the system performance at different combinations of the feed flow rate ($\dot{V}_{in}$) and of the ratio of the flow rates of the filtrate outlet ($\dot{V}_f$) and the concentrate outlet ($\dot{V}_c$). FIG. 6A presents the red blood cell collection percentage of the device, and FIG. 6B presents the red blood cell concentration factor of the device. These measurements were performed with 500 mL of 10-fold diluted porcine blood. The selected range of feed flows was centered at 30 mL/min or 1.8 L/hour. The RBC concentration efficiency was the best at low inlet flow velocity and exceeded 80% at about 20 mL/min. It exceeded 70% up to 60 mL/min at a ratio of 1 ($\dot{V}_f = \dot{V}_c$). However, RBC concentration at higher ratios of the exit flows dropped below 50%. RBC concentration factor is the ratio of RBC concentration for the concentrate outlet flow relative to that of the input flow; for example, blood flowing in at a hematocrit of 10% (i.e., 10-fold diluted blood) that was reconstituted to a hematocrit of 20% (i.e., 5-fold diluted blood) at the concentrate outlet would yield a concentration factor of 2.

The highest concentration of RBCs in the collector was achieved at the highest elution flow ratios, where the same amount of the cells was eluted in smaller volume. In these measurements, the operation started after the acoustic cavity was filled with the sample and finished after the system was flushed with saline, chasing the blood sample. However, the removal of the RBCs from the system became inefficient (under 80%) at high elution flow ratios when the feed velocity was high. Typically, 50 mL of blood diluted with saline up to 500 mL was used in the experiments. The ability to recover RBCs from diluted samples proved system applicability for blood component washing. This application is typical of blood banking processes and is also the field where maximal flow rates may be demanded. However, this protocol is not optimal for the applications that demand the highest hematocrit. In this case, the best approach is to perform the processing at low inlet flow velocity and high ratio of the exit flow rates. Note that although different applications may use different protocols, every protocol can be performed on the same system due to the universality of the present systems and devices.

The collection performance of the system at different dilutions at the "optimal" flow conditions from the flow matrix were evaluated, chosen to be 10 mL/min inflow and an outflow ratio of 4, to achieve both high cell collection and a high concentration factor, as shown in Table 2 below.

TABLE 2

Summary of Varying Dilution Results (10 mL/min inflow and ratio of 4)

| Whole Blood Dilution Factor | 10× | 7× | 5× | 3× |
| --- | --- | --- | --- | --- |
| Inflow RBC Concentration (×10$^9$/mL) | 0.69 | 1.19 | 1.67 | 2.75 |
| Percent of RBCs Collected | 99% | 85% | 64% | 47% |
| Concentration Factor | 5.3 | 3.9 | 2.9 | 2.0 |

The dilution factor was decreased until the cell collection dropped below 50%, which occurred when the inflow blood sample was diluted 3-fold. The performance degraded because of overloading the concentrate outlet with separated RBCs. However, this performance can be improved with further optimization, as removing the cells from the system faster could yield higher cell collection. Low dilutions of blood are important in plasma preparations.

Testing to Measure Lipid Filtration Efficiency

Blood/lipid isolation experiments were conducted using the diluted porcine blood and a 0.75% safflower oil emulsion. The mixture consisted of 25 mL of the oil emulsion, 25 mL of whole porcine blood, and 200 mL of PBS, resulting in an end RBC concentration of approximately 4 vol %. After gentle mixing of the solution to ensure homogeneity, the acoustophoretic system was prepared for the twenty minute test. The mixture was pumped through the system using a peristaltic pump that passed the blood/lipid mixture from the inflow reservoir through the inlet of the device at a rate of 16 mL/min. The concentrate outlet draw was set to 1 mL/min, resulting in a flow of 15 mL/min into the outflow reservoir of the system. Visual observations were made using a Proscope HR USB camera from Bodelin (Lake Oswego, Oreg.) to document lipid aggregation on the top polycarbonate window. Complete blood counts were obtained using a VetScan HMS hematology analyzer from Abaxis Co. (Union City, Calif.).

An experiment for the effectiveness of collecting and concentrating lipid particles was performed by first separating the lipids from blood to evaluate the experimental measurement. A 0.2% lipid suspension in saline was created using pork belly fat (chosen as the best simulant for fat collected from a surgical field) that was procured from a local butcher. The lipid suspension was then passed through a UpiGuard® SB transfusion filter from Haemonetics (Braintree, Va.) with 40 µm size cutoff to simulate the actual procedure used in a comparative Cell Saver protocol. This step was introduced because systems for surgical blood treatment include a similar filter to remove clots and bone fragments, which are typical admixtures in the blood, collected from the surgical field, and thus contaminate the RBC fraction either with centrifugal or acoustic method. The filter removed large particles that constitute most of the fat after extensive homogenization (the particles are expected to be larger in real surgery); less than 10% of the initial load (<0.02% total content) remained in the diluted blood sample (compare images A and B in FIG. 7). The final mixture was sent into the acoustophoretic device. Once collected, the lipids were dried and weighed. Weighing was used because radioactive labels could not be used due to the lack of laboratories still practicing the same. Fluorescence-based analysis cannot be used with blood products because of background interference, and fluorescence is also not a quantitative method.

FIGS. 7A-7E illustrate a lipid image analysis at 40× magnification. The leftmost image in the top row (FIG. 7A) shows lipid particles in saline immediately after spike. The middle image in the top row (FIG. 7B) shows the lipid particles in saline after filtration through a physical filter. The rightmost image in the top row (FIG. 7C) shows the lipid particles in saline after undergoing acoustic filtration according to the present disclosure. The left side image in the bottom row (FIG. 7D) shows the lipid particles in saline after agglomerating and rising to a lipid collection trap at the top of a flow chamber. The right side image in the bottom row (FIG. 7E) shows a top view of the lipid collection trap after filtration of the lipid particles according to the present disclosure.

Treatment by the acoustic standing wave system produced two effects. First, an additional part of the lipids was removed (see FIG. 7D and FIG. 7E). These particles were larger than those in the injected spike due to acoustics-induced clumping. Second, although the sizes of the particles that penetrated through the system and were found in the filtrate were similar to the sizes of the particles right after the LipiGuard filtration, the proportion of larger particles was smaller after acoustic treatment. This effect is difficult to see in FIG. 7B and FIG. 7C, but was noticeable after visual comparison of multiple frames. Quantitation of the lipid content gives 60±5 mg, 65±15 mg, and 150±25 mg in the fraction extracted from the lipid collection trap, from the resonator volume, and from the filtrate, respectively. In total, this constitutes 275±45 mg of lipids, which coincides within the error with the spiked load of 250±20 mg. On the one hand, this gives no detectable lipid load in the fraction collected through the concentrate outlet (neither by subtraction nor by the direct measurement). On the other hand, about half of the lipid load passed through the acoustic filter and collected in the filtrate outlet. However, this fraction is mostly void of particles larger than the size of cells; therefore, the remaining lipid particles are too small to cause microemboli. Most of the particles with sizes in the range of 10 to 40 microns were acoustically removed.

Additional Experiments

Next, full blood analyses were performed on all harvested streams from the device of FIG. 4 to quantify the blood components in each stream and to determine the viability of the harvested RBC. This testing included characterization of the blood fractions for cell composition and biochemical parameters. A Beckman Coulter Ac-t diff Hematology Analyzer was used, which features a high throughput and low reagent requirements with equivalent linearity and reliability in comparison with other equipment. From the hematology analyzer, the content of red and white blood cells (WBC), platelets, and free hemoglobin was determined. It was found that WBCs and RBCs were isolated in the same fraction, and free hemoglobin content did not change as a result of acoustic treatment.

In particular, experiments were performed to explore the effectiveness of the device to filter lipids from blood, the potential of hemolysis, and other negative effects such as platelet aggregation, as well as the success of reinfusion of filtered blood in a porcine surgical model. Again, the tests were completed with porcine blood purchased from Hemostat Laboratories, CA. All experiments using fresh porcine blood were collected by an animal care facility according to IACUC approved protocols and donated to the study. Blood was stored in EDTA (ethylene diamine tetraacetic acid) prepared tubes and used within two weeks of collection. The whole porcine blood was diluted by a factor of 10 using phosphate buffered saline (PBS), purchased from Fisher Biosciences (Agawam, Mass.) so that visual observations of particle capture could be conducted.

Figure 8:
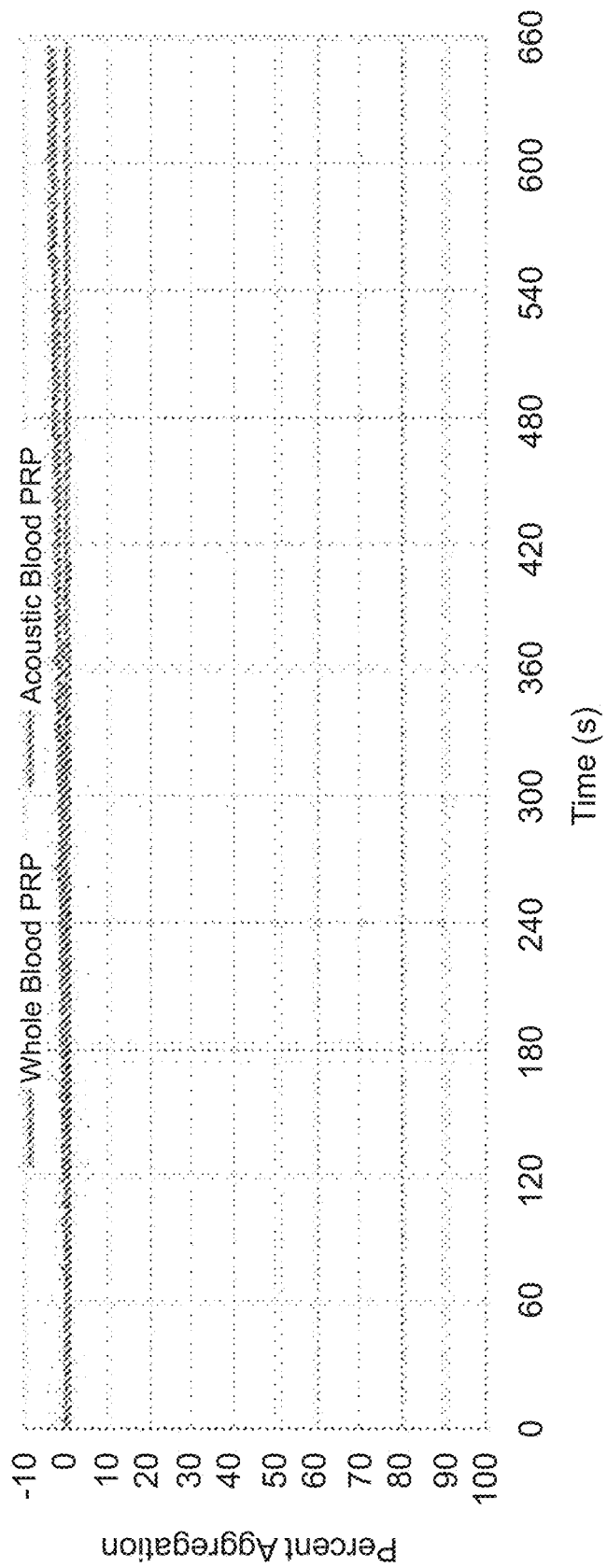
FIG. 8 is a graph illustrating the acoustic effect on the blood components, namely platelet aggregation in blood that was examined after separation and reconstitution according to the present disclosure. The y-axis is percent aggregation, and runs from −10 at the top to 100 at the bottom in intervals of 10. The x-axis is time in seconds, and runs from 0 at the left to 660 at the right in intervals of 60.

Fresh porcine blood was collected and run through the device before being reconstituted. To assess the viability of platelets after sonic capture, blood was treated with thrombin. Percent of platelet aggregation was measured with a Bio Data Platelet PAP 8-E Aggregation Profiler. Platelet activation and aggregation would be a cause for concern, as energy put into the system could cause the blood to clot. FIG. 8 is a graph showing the platelet aggregation of the blood after processing in the acoustophoretic system and the platelet aggregation of unprocessed blood. As can be seen in the date in FIG. 8, no discernable evidence of aggregation/coagulation was found, which shows that the acoustic energy used did not have a deleterious effect on the blood components.

Next, biochemical characterization was performed. Porcine ELISA kits were used to determine levels of various biological markers in processed and unprocessed blood.

Five ELISA kits were used for this study: (1) Porcine Haptoglobin ELISA Kit from GenWay Biotech (San Diego, Calif.); (2) Porcine LDH ELISA Kit from Novateinbio (Woburn, Mass.); (3) Porcine D-Dimer ELISA Kit from US Biological (Salem, Mass.); (4) Porcine IL-6 ELISA Kit from Sigma Aldrich (St. Louis, Mo.); and (5) Porcine TNF-α ELISA Kit from Fisher Scientific (Waltham, Mass.).

Figures 9A, 9B:
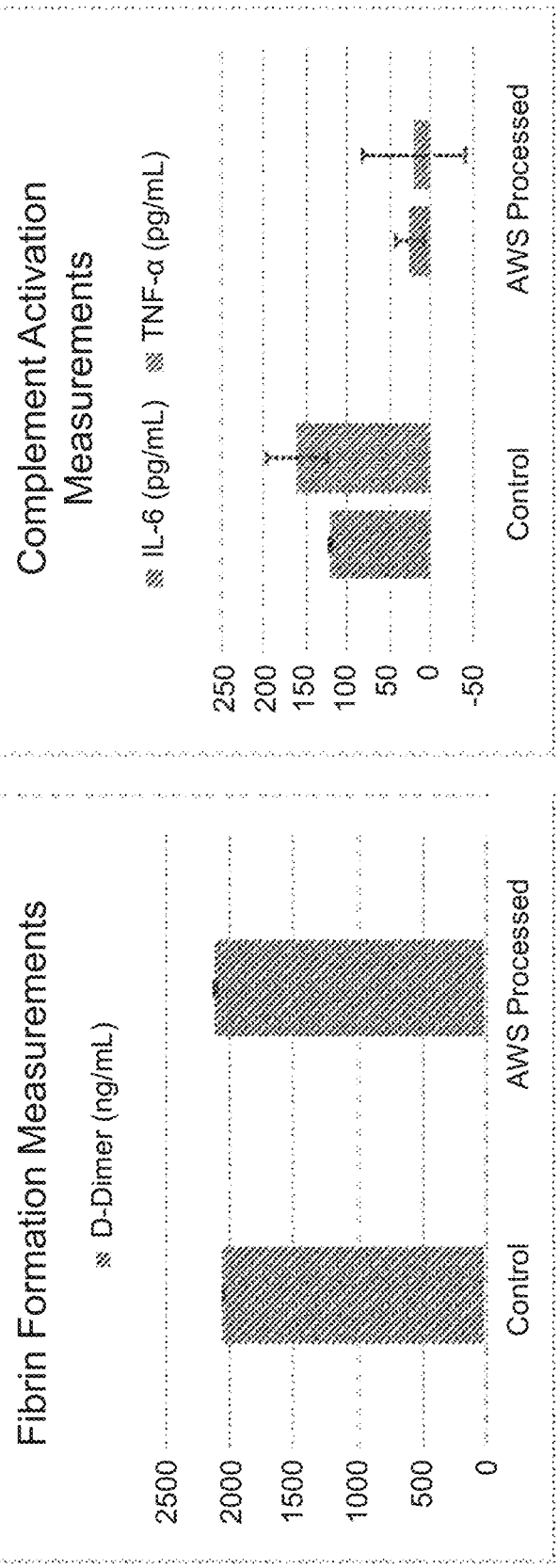
FIG. 9A is a graph illustrating the acoustic effect on the blood components, namely fibrin formation in (i) control blood and (ii) blood that was processed through an acoustic standing wave system. The y-axis is in nanograms per milliliter (ng/mL), and runs from 0 to 2500 in intervals of 500.
FIG. 9B is a graph illustrating the amount of activated complements on the blood of FIG. 9A. The y-axis is in picograms per mL (pg/mL), and runs from −50 to 250 in intervals of 50. IL-6 is the left-hand bar and TNF-α is the right-hand bar for both "control" and "AWS processed".

FIG. 9A shows the D-Dimer formation of the acoustically separated blood versus the control blood. The ELISA measurement demonstrated no significant change in D-Dimer levels, evidencing that the acoustic filtration did not cause thrombus formation. Potential activation of the complement pathway was also examined by exploring IL-6 and TNF-α release. FIG. 9B presents the results, which show that in comparison with the non-acoustically processed blood (i.e., the control blood), there was a decrease of 79% in the IL-6 concentration and 87% in the TNF-α concentration. These results signify that no inflammatory activation occurred due to the acoustic capture of the cells. In fact, the acoustically processed blood showed a much lower propensity towards inflammatory activation than the control sample that was run through a physical filter, thus evidencing additional advantages of the use of acoustophoresis over conventional filters. The results of these ELISAs are also presented in Table 3 below.

Figure 10:
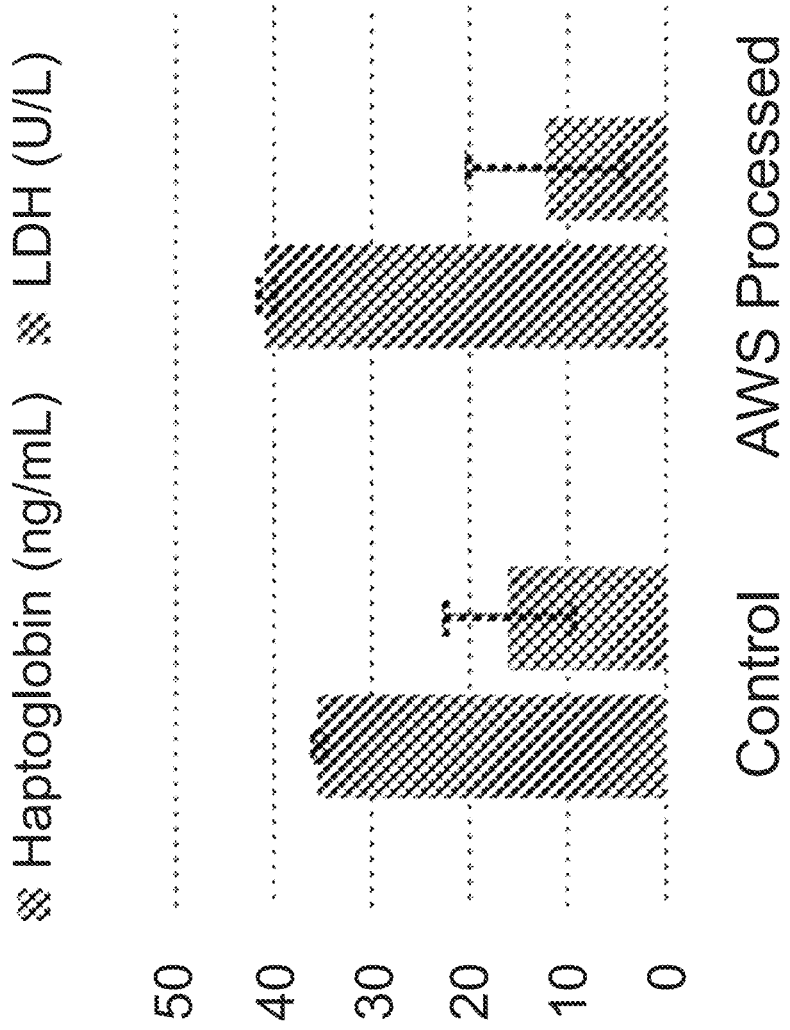
FIG. 10 is a graph measuring hemolysis of red blood cells in (i) control blood and (ii) blood that was processed through an acoustic standing wave system. The y-axis runs from 0 to 50 in intervals of 10. For haptoglobin, the units are ng/mL. For LDH, the units are Units per liter (U/L). Haptoglobin is the left-hand bar and LDH is the right-hand bar for both "control" and "AWS processed".

Lactate dehydrogenase and haptoglobin ELISAs were also performed on recombined treated blood (i.e., AWS processed blood) and compared to non-treated blood (i.e., control blood). These tests were performed to ensure that the acoustic energy was not causing the red blood cells to rupture. The results are presented in FIG. 10, which shows that there was a slight increase of 15% in haptoglobin levels, while LDH levels decreased by 2.5%. Thus, neither measurement demonstrated hemolysis was occurring after acoustic processing, which was consistent with a lack of hemolysis upon microscopic inspection of the RBCs (data not shown). Again, the results of these ELISAs are also presented in Table 3 below.

As explained above and as can be seen in Table 3 below, measurements of the haptoglobin and LDH levels did not reveal hemolysis after acoustic processing. Measurements of the platelet function (data not shown) and D-Dimer content did not reveal activation of coagulation. Measurements of TNF-α and IL-6 levels did not show activation of inflammatory cascades, but rather showed a decrease in level after processing. None of the measurements indicated that the exposure to the acoustic standing wave field created any damage to the blood components. The highest hematocrit achieved was up to 50%. This level is considered currently sufficient for transfusion.

TABLE 3

Summary of ELISA Measurements

|  | Control | AWS Processed | Change |
|---|---|---|---|
| Haptoglobin (ng/mL) | 35.5 | 40.9 | +15% |
| LDH (U/L) | 16.1 | 12.3 | −24% |
| D-Dimer (ng/mL) | 2058.7 | 2119.9 | +3% |
| IL-6 (pg/mL) | 120.3 | 25.2 | −79% |
| TNF-α (pg/mL) | 159.9 | 20.6 | −87% |

Finally, the effect of acoustically filtered blood that was auto-transfused into a porcine undergoing surgery was examined. The purpose of this test was to determine the physiological effect of processing erythrocytes through the acoustophoretic device and observe any change in the subject's vitals after receiving a transfusion of acoustically processed blood.

Two Yorkshire female pigs weighing ~20 kg were used for the study. The day of the procedure, the pigs were given a single pre-anesthetic dose of Telazol 5 mg/kg, Ketamine 25 mg/kg, and Xylazine 2.5 mg/kg (TKZ) at 1 cc/20 kg. The animals were then endotracheally intubated and maintained under general anesthesia with continuous Isoflurane. Once anesthetized, carotid artery cut-down was performed to allow for invasive hemodynamic monitoring. After adequate hemodynamic monitoring was set up and baseline measurements obtained, the animals were drained of 240 mL of whole blood, which was mixed with EDTA to prevent clotting. The amount of blood removed was no more than ~15% of the animals' total blood volume, thereby preventing shock and hemodynamic instability. Of the drained volume, the AWS processing occurred in two steps to get fluid back to the animal as quickly as possible. First, 125 mL of whole blood was diluted with 875 mL of normal saline to create a 7:1 saline to blood dilution. This dilution was then processed through the acoustophoretic system. Once the first batch was completed, the collected 200 mL blood product was transfused back to the animal, while a second portion of the blood, which was diluted at the same ratio, was processed. A total of 400 mL of blood product was transfused back into each animal. Multiple hemodynamic measurements were obtained during the procedure including temperature, systolic blood pressure (SBP), and mean arterial pressure (MAP) and compared to baseline measurements. Multiple blood samples were collected at 30 minute intervals after the initial blood collection as well as 0.5 minutes after each transfusion to determine the hemoglobin/hematocrit (H/H). Three hours after blood transfusion, the animals were euthanized using a single dose of euthanasia solution Fatal Plus® from Vortech (Dearborn, Mich.).

Figure 11:
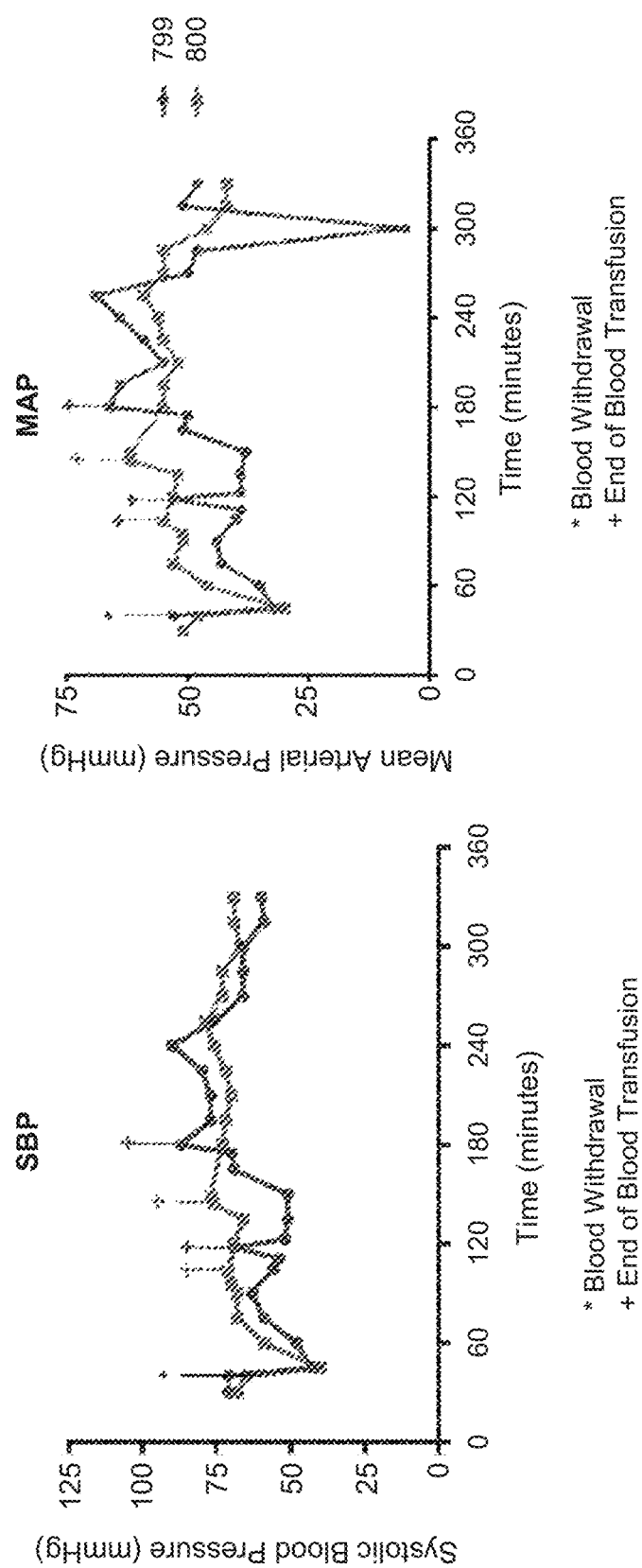
FIG. 11A is a graph illustrating the effect on the systolic blood pressure of blood filtered by acoustophoresis in accordance with the present disclosure that was auto-transfused into two porcines undergoing surgery. The y-axis is in mmHg, and runs from 0 to 125 in intervals of 25.
FIG. 11B is a graph illustrating the effect on mean arterial pressure of the processed blood. The y-axis is in mmHg, and runs from 0 to 75 in intervals of 25.

FIG. 11A presents the pigs' SBP levels, while FIG. 11B presents the pigs' MAP levels. As can be seen in FIG. 11A and FIG. 11B, SBP and MAP decreased soon after exsanguination in both animals. A rise in both is seen prior to the transfusions, which is secondary to the animals' own compensatory drive. However, after each transfusion, there was an increase in these values, suggestive that the animal does respond to the blood being administered. Towards the end of the procedure, a decrease in the blood pressure can be seen, which is most likely due to the animals' prolonged time under general anesthesia. All in all, FIG. 11A and FIG. 11B show, respectively, that the animals' SBP and MAP were not significantly affected by the acoustically processed blood versus the control.

Figure 12:
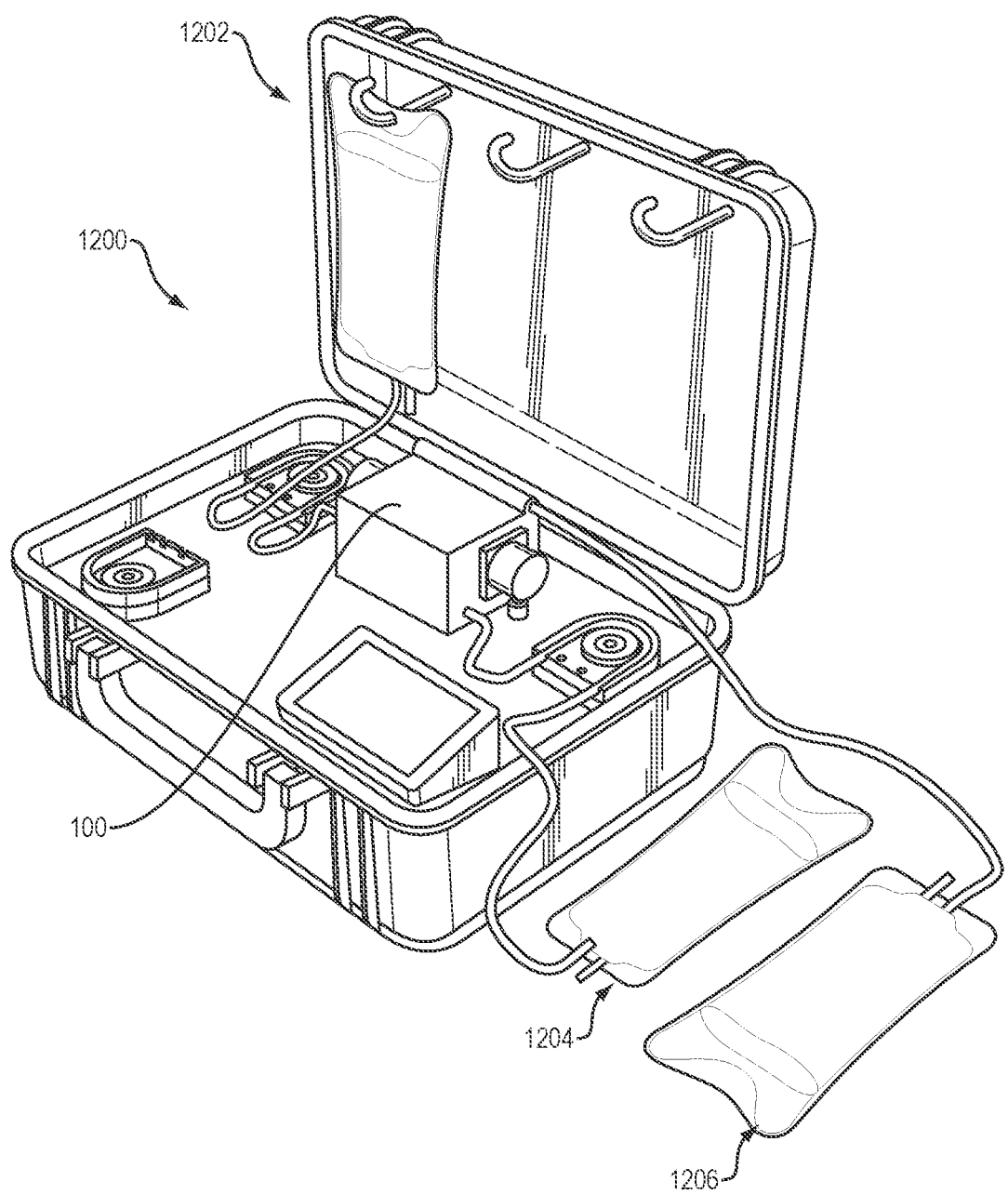
FIG. 12 is an image that illustrates a first exemplary embodiment of a portable, autonomous acoustophoretic system according to the present disclosure. The system includes a battery-powered acoustophoretic device according to the present disclosure. Also visible is tubing and at least two separate bags (the first to provide a source of blood to the device, the second to receive separated blood components). The various components are housed in a portable container, such as the suitcase shown here.

Turning now to FIG. 12, an illustrative embodiment of an acoustophoretic system 1200 is depicted. The system generally includes an acoustophoretic device according to the present disclosure, such as acoustophoretic device 100 depicted in FIG. 1 and FIG. 2. For many of the applications described below, it would be advantageous for the system 1200 to be both autonomous and portable. The portability of the system 1200 can be achieved by making the acoustophoretic device battery-powered, such that in emergency or force majeure situations, patient treatment can be performed under field conditions void of electrical power or ability to transport heavy equipment to the point of care.

It is contemplated that the system 1200 can be a platform-based system, such as a system housed within a portable briefcase 1202 as is depicted in FIG. 12. It is further contemplated that all components of the system in contact with blood and its products will be united into a single disposable unit, including input and output lines integrated with the acoustic resonator, and replaced as a whole between preparations of different blood batches. The disposable units will be sealed and sterilized to prevent contamination and infections and will be installed in only one way to prevent human error. Additionally, the system performance may be enhanced by using different disposable assemblies optimized for specific procedures (e.g., lipid extraction, blood cell isolation, cell washing, blood banking). Such a system is therefore sufficiently flexible to be applied to blood treatment operations in both routine and contingency situations. As explained above, the devices can include a container for collecting the isolated materials (e.g., red blood cells, lipids). The container collecting the product after processing will be designed to be detachable once the operation is complete, automatically sealed upon removal to maintain the sterility of the material, and usable at temperatures as low as −80° C. Here, the container 1204 is a flexible bag. A separate flexible bag is also used as the input reservoir 1206 of blood.

Again, it would be desirable to construct every component of the systems and devices described herein that come in contact with blood to be part of a sterile, disposable assembly. In particular, there are at least two options for designing the ultrasonic transducer-reflector pair to be sterile and disposable. First, the transducer-reflector pair can be integrated as part of the disposable assembly. The advantages of such a design include the most efficient acoustic performance by coupling the transducer with, for example, a molded flow chamber of a Class 6 material and the means to isolate the transducer surface from the contact with blood. Another alternative option is to develop a flow chamber that will be an insert into a transducer-reflector assembly. In this case, the introduction of additional layers will decrease the acoustic performance, but this option is cheaper than the first option, which is a major driver for disposable applications.

The design of the systems and devices disclosed herein incorporate the peripherals used to perform practical applications such as cell washing, cryoprotectants manipulating, and removal of foreign components that may contaminate blood collected from wounds. As explained above, these systems and devices are integrated, isolated from the environment, and disposable.

The total volume of suction blood to be filtered during a bypass surgery can approach 1 liter to 1.5 liters, which can be collected within 45 minutes. The systems and devices disclosed herein are capable of processing this amount. In particular, these systems and device can handle about 20 mL/min to about 30 mL/min, and up to as high as 2 L/hour or more, of whole undiluted blood flow (i.e., up to about 20 L/hour of 10-fold diluted blood flow). This blood is not typically re-transfused to the patient right away, but rather returned at the end of the operation.

Usual practice recommends ≥80%, of the patient's RBC concentration for transfusion, although as low as 50% can be acceptable. Normal RBC concentration is 40-45% by volume. The systems and devices of the present disclosure are capable of achieving 32-36% RBC (80% of normal hematocrit) in concentrates intended for transfusion. As to the products for storage, especially at −80° C., the RBC concentration is less important, because the product will be subjected to additional washing that accompanies deglycerolization; the RBC concentration can be increased at this stage the same way it will be done for a transfusion product.

During prolonged storage at 4° C., RBC concentrates acquire 'storage lesions.' The suspending solvent composition changes due to RBC metabolism and degradation of some of the cells (e.g., concentrations of ammonia, phosphate, potassium, and free hemoglobin increase as well as the solvent's acidity). RBCs also experience morphological shape changes: their membranes stiffen, the cells change shape, become stickier, and more tightly bind oxygen. These changes, which may impair clinical outcomes after transfusion, can be corrected to a large extent by washing RBCs in proper solvents. Also, washing out-of-date (i.e., 1-4 weeks after their expiration dates) RBCs with a cell saver device makes them usable and safe for a patient. However, washing RBC concentrates prior to transfusion is not a common practice in a blood bank and is considered a labor intensive process because of the complexity involved. For example, using a cell saver to treat expired RBC concentrates is not difficult to implement during a cardiac surgery, when a cell saver is running anyway, but it would be too much effort in common blood banking practice.

RBC concentrates can also be stored at −80° C., and can be preserved for decades at this temperature. Donor blood can be stored at 4° C. until the expiration date, and then cryopreserved, where it will be still viable for decades. Typically, only RBCs are frozen. Preparation of blood for deep freezing or for transfusion after thawing can include the addition or removal of a cryoprotectant (glycerol). These operations also involve washing the RBCs in an appropriate solvent, and the recovery achieves 94%. The quality of the recovered RBCs primarily depends on the deglycerolization washing process, on the biologic variation among RBC units, and on the pre-freeze and post-thaw storage times.

There are several options to combine the disclosed multidimensional ASW process with a washing procedure in which the red blood cells are washed with a washing solvent to remove undesired admixtures therefrom. The first option is to dilute the whole blood with a washing solvent. The diluted blood is then sent through an acoustic filtration device to concentrate the red blood cells in the now-diluted blood in accordance with the methods already disclosed herein. A second option is to first send the whole blood through the acoustic filtration device to trap red blood cells within the acoustic standing wave (without the RBCs concentrating and falling out of the standing wave). The washing solvent is then sent through the flow chamber to wash the RBCs. An intermediate approach is to combine the flows of undiluted whole blood and the washing solvent into a single flow, which can be flowed through the flow chamber at a flow rate of at least 4.5 m L/m in, and then performing the RBC separation in accordance with the methods already disclosed herein. This intermediate approach is depicted in FIG. 4. Examples of washing solvents include water and saline.

Integration of a washing option with the systems and devices of the present disclosure can include the presence of a subsystem to inject different solvents in a controlled way into undiluted whole blood. In this way, a single system/device can be used for blood, in addition to the various other techniques discussed herein. In general, the systems/devices are capable of injecting and mixing aqueous solvents as well as high concentration glycerol solvents. After the procedures, the blood components may be thoroughly tested with biochemical assays.

The systems and devices of the present disclosure may also be optimized for platelet isolation from blood. This function may involve several centrifugation steps in conventional machines, because of the small difference in properties between RBCs and platelets. However, using ASW technology, several simpler options are available. First, the ASW systems/devices may employ different acoustic frequencies to enhance selectivity in different scale domains. As the acoustic force depends on the size of the cells (see the equation for acoustic radiation force above), larger cells are held more strongly than smaller cells at a fixed frequency. Therefore, this technique can be used to isolate platelets (2-3 µm), which are smaller than RBCs or leukocytes (6-8 µm and 10-15 µm, respectively). An ASW system will perform better in prolonged or repeated processes, because of its minimal (if any) influence on the cell vitality. This is especially important in the treatment of platelets to avoid their activation. Because of minimal acoustic damage, multiple cycles can be implemented to improve separation. A second option for platelet isolation is to employ specialty fluidics. The acoustic and hydrodynamic forces are proportional to the third and second power of particle radius, respectively. Hence, variation of the transducer power in combination with the flow rate can be used for separation. Finally, a third option is to introduce macroscopic changes using biological differences, which in turn will modify susceptibility to acoustic force. For example, dead and live cells have different membrane permeability. Therefore, manipulation with osmotic pressure may introduce differences in sizes between the dead and live cells. Red blood cells accumulate organic compounds that intercalate the membrane and change its rigidity as well as the overall size and shape of erythrocytes. This difference can be also exploited for fractionation.

Figure 13:
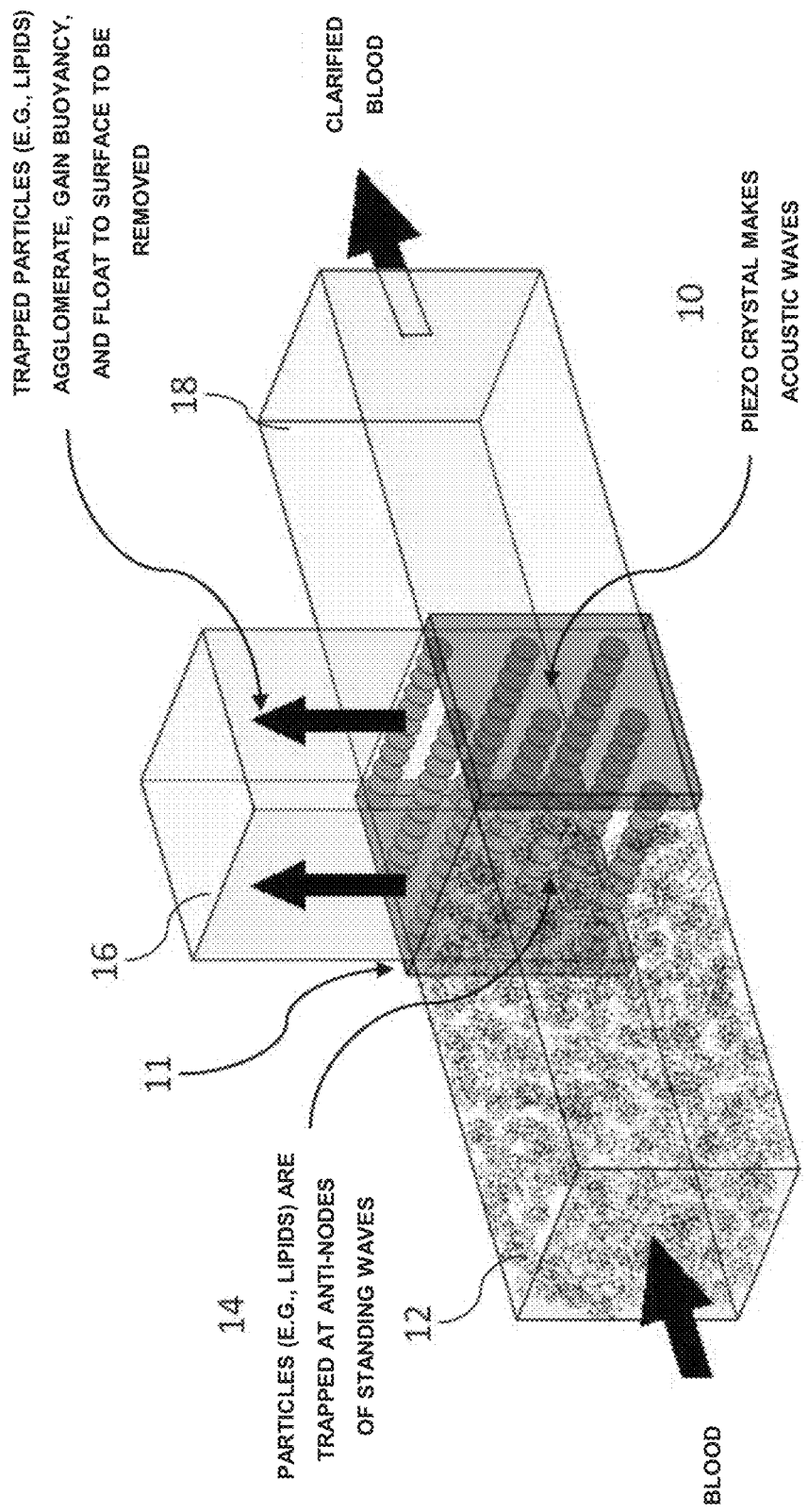
FIG. 13 is a diagram illustrating an acoustophoretic separation method according to the present disclosure for a particle or blood component (e.g., lipids) less dense than a host fluid (e.g., blood).

A diagrammatic representation of an acoustic chamber for removing lipids or other lighter-than-blood material is shown in FIG. 13. Excitation frequencies typically in the range from hundreds of kHz to 10 s of MHz are applied by transducer 10. One or more standing waves are created between the transducer 10 and the reflector 11. Incoming blood containing blood components enters at inlet 12. Particles (e.g., lipids) are trapped in standing waves at the pressure anti-nodes 14 where they agglomerate, aggregate, clump, or coalesce, and, in the case of buoyant material, float to the surface and are discharged via a lipid collection trap 16 located above the flow path and above the acoustic standing wave. Clarified fluid (e.g., blood) is discharged at filtrate outlet 18. The acoustophoretic separation technology can accomplish multi-component particle separation without any fouling at a much reduced cost.

Figure 14:
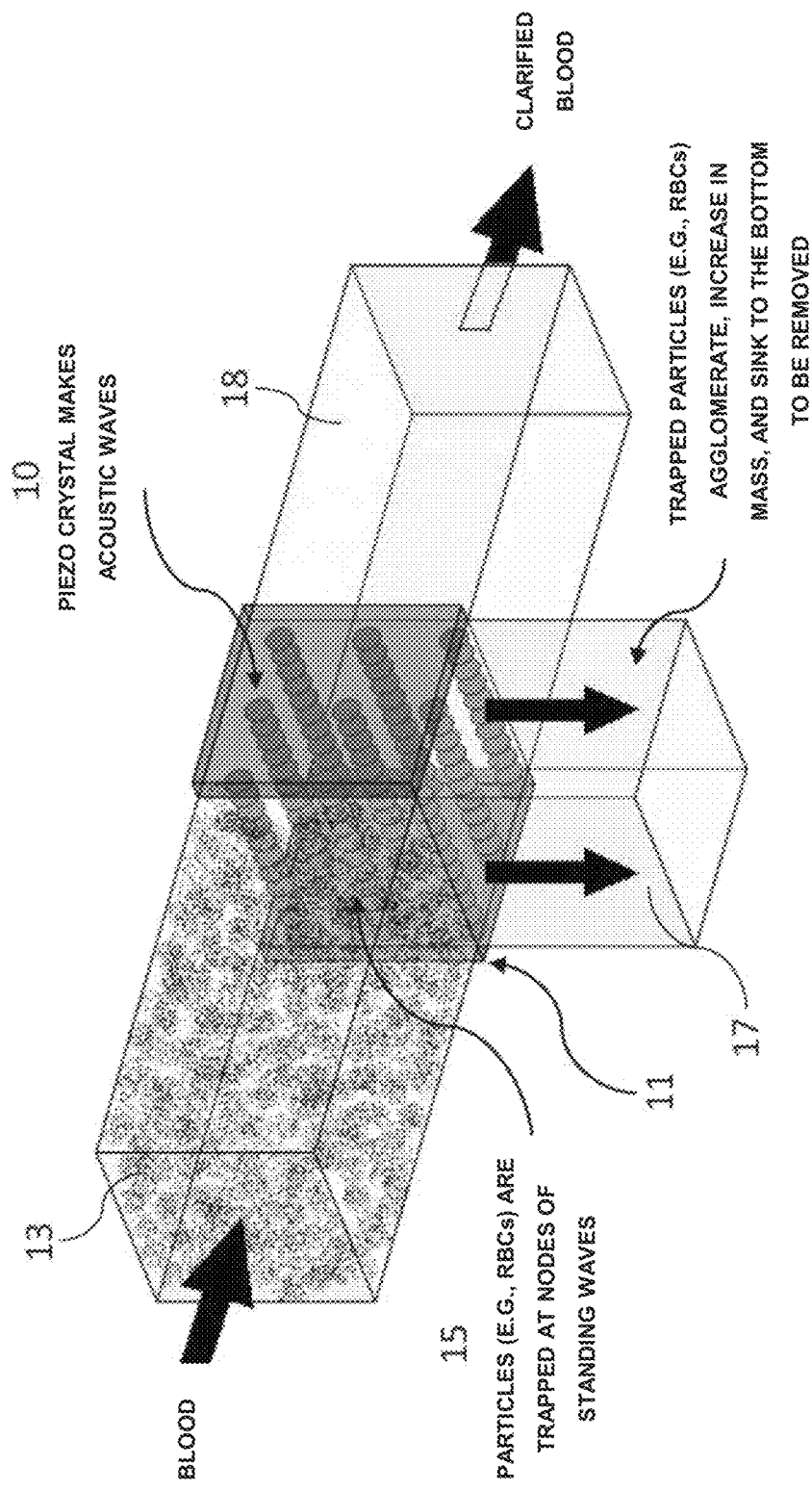
FIG. 14 is a diagram illustrating an acoustophoretic separation method according to the present disclosure for a particle or blood component (e.g., red blood cells) denser than a host fluid (e.g., blood).

A diagrammatic representation of an acoustic chamber for removing blood cells or other heavier-than-blood material is shown in FIG. 14. Excitation frequencies typically in the range from hundreds of kHz to 10 s of MHz are applied by transducer 10. One or more standing waves are created between the transducer 10 and the reflector 11. Incoming blood enters through inlet 13. Particles (e.g., blood cells) are trapped in standing waves at the pressure nodes 15 where they agglomerate, aggregate, clump, or coalesce, and, in the case of heavier material, sink to the bottom and are discharged via a concentrate outlet 17 located below the flow path and below the acoustic standing wave. Clarified fluid (e.g., blood) is discharged at filtrate outlet 18.

As previously explained, the ultrasonic transducer and reflector are located on opposite sides of the acoustic chamber. In this way, one or more acoustic standing waves are created between the ultrasonic transducer and reflector.

Prior to discussing further optimization of the devices, it is helpful to provide an explanation now of how multi-dimensional acoustic standing waves are generated. The multi-dimensional acoustic standing wave used for particle collection is obtained by driving an ultrasonic transducer at a frequency that both generates the acoustic standing wave and excites a fundamental 3D vibration mode of the transducer crystal. Perturbation of the piezoelectric crystal in an ultrasonic transducer in a multimode fashion allows for generation of a multidimensional acoustic standing wave. A piezoelectric crystal can be specifically designed to deform in a multimode fashion at designed frequencies, allowing for generation of a multi-dimensional acoustic standing wave. The multi-dimensional acoustic standing wave may be generated by distinct modes of the piezoelectric crystal such as a 3×3 mode that would generate multidimensional acoustic standing waves. A multitude of multidimensional acoustic standing waves may also be generated by allowing the piezoelectric crystal to vibrate through many different mode shapes. Thus, the crystal would excite multiple modes such as a 0×0 mode (i.e. a piston mode) to a 1×1, 2×2, 1×3, 3×1, 3×3, and other higher order modes and then cycle back through the lower modes of the crystal (not necessarily in straight order). This switching or dithering of the crystal between modes allows for various multidimensional wave shapes, along with a single piston mode shape to be generated over a designated time.

Some further explanation of the ultrasonic transducers used in the devices, systems, and methods of the present disclosure may be helpful as well. In this regard, the transducers use a piezoelectric crystal, usually made of PZT-8 (lead zirconate titanate). Such crystals may have a 1 inch diameter and a nominal 2 MHz resonance frequency, and may also be of a larger size. Each ultrasonic transducer module can have only one crystal, or can have multiple crystals that each act as a separate ultrasonic transducer and are either controlled by one or multiple amplifiers. The crystals can be square, rectangular, irregular polygon, or generally of any arbitrary shape. The transducer(s) is/are used to create a pressure field that generates forces of the same order of magnitude both orthogonal to the standing wave direction (lateral) and in the standing wave direction (axial).

Figure 15:
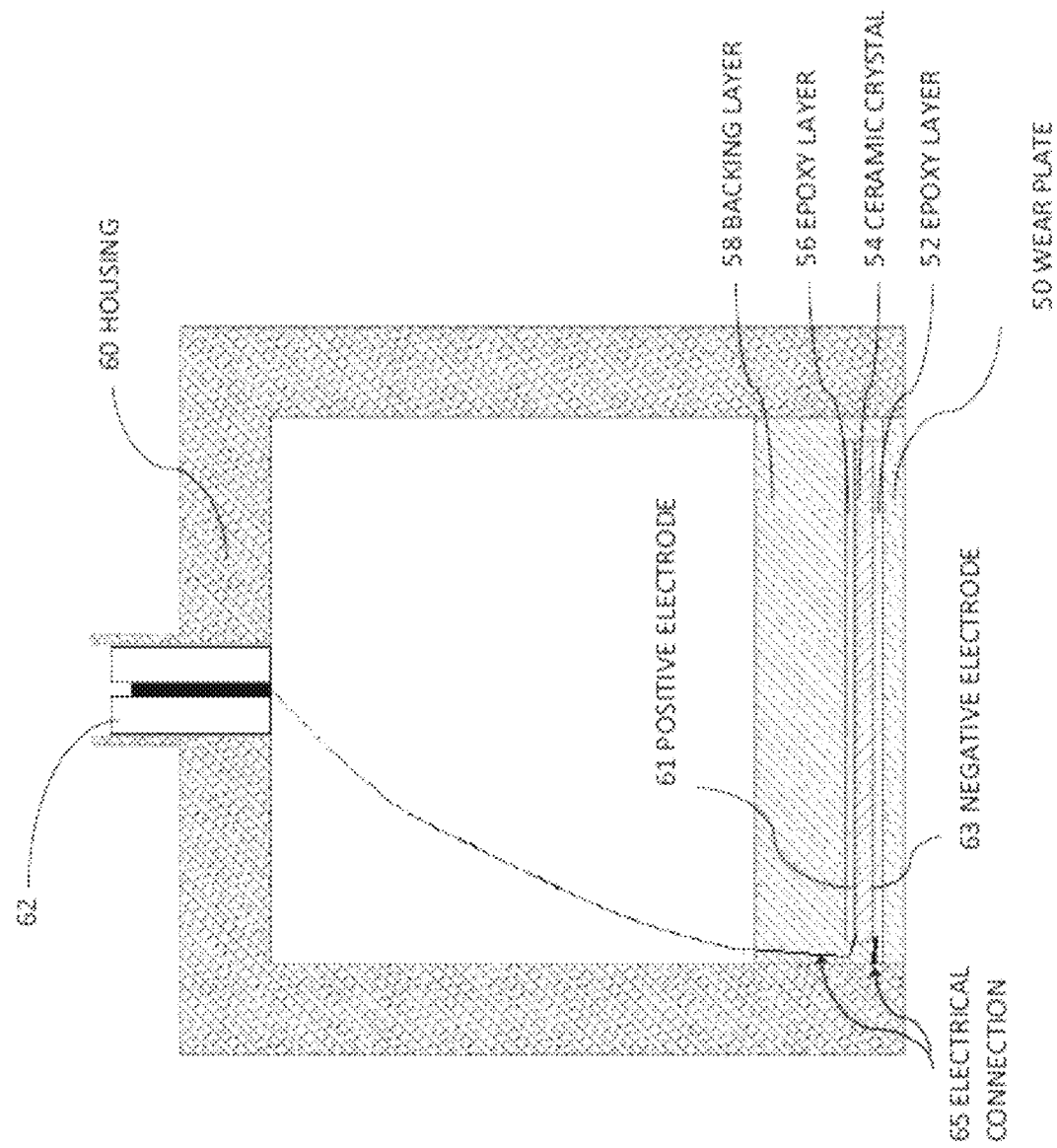
FIG. 15 is a cross-sectional diagram of a conventional ultrasonic transducer.

FIG. 15 is a cross-sectional diagram of a conventional ultrasonic transducer. This transducer has a wear plate 50 at a bottom end, epoxy layer 52, ceramic crystal 54 (made of, e.g. PZT), an epoxy layer 56, and a backing layer 58. On either side of the ceramic crystal, there is an electrode: a positive electrode 61 and a negative electrode 63. The epoxy layer 56 attaches backing layer 58 to the crystal 54. The entire assembly is contained in a housing 60 which may be made out of, for example, aluminum. An electrical adapter 62 provides connection for wires to pass through the housing and connect to leads (not shown) which attach to the crystal 54. Typically, backing layers are designed to add damping and to create a broadband transducer with uniform displacement across a wide range of frequency and are designed to suppress excitation at particular vibrational eigenmodes. Wear plates are usually designed as impedance transformers to better match the characteristic impedance of the medium into which the transducer radiates.

Figure 16:
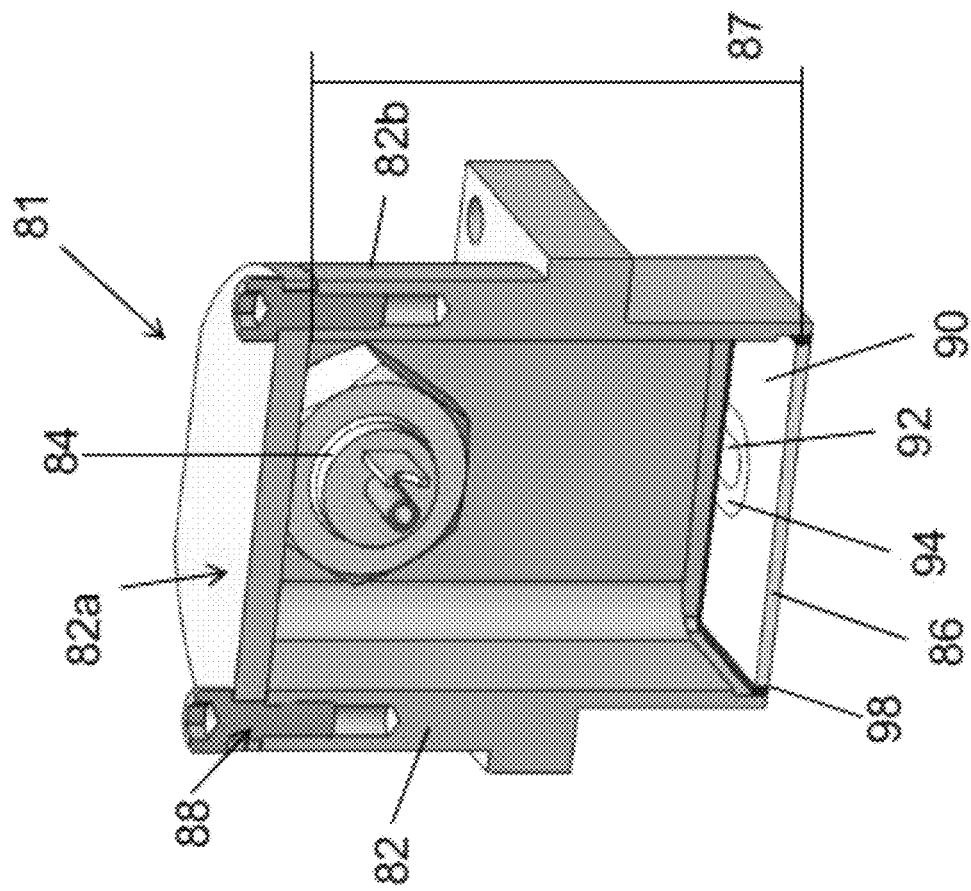
FIG. 16 is a cross-sectional diagram of an ultrasonic transducer of the present disclosure. An air gap is present within the transducer, and no backing layer or wear plate is present.

FIG. 16 is a cross-sectional view of an ultrasonic transducer 81 of the present disclosure. Transducer 81 is shaped as a disc or a plate, and has an aluminum housing 82. The piezoelectric crystal is a mass of perovskite ceramic crystals, each consisting of a small, tetravalent metal ion, usually titanium or zirconium, in a lattice of larger, divalent metal ions, usually lead or barium, and O2-ions. As an example, a PZT (lead zirconate titanate) crystal 86 defines the bottom end of the transducer, and is exposed from the exterior of the housing. The crystal is supported on its perimeter by a small elastic layer 98, e.g. silicone or similar material, located between the crystal and the housing. Put another way, no wear layer is present. In particular embodiments, the crystal is an irregular polygon, and in further embodiments is an asymmetrical irregular polygon.

Figure 17:
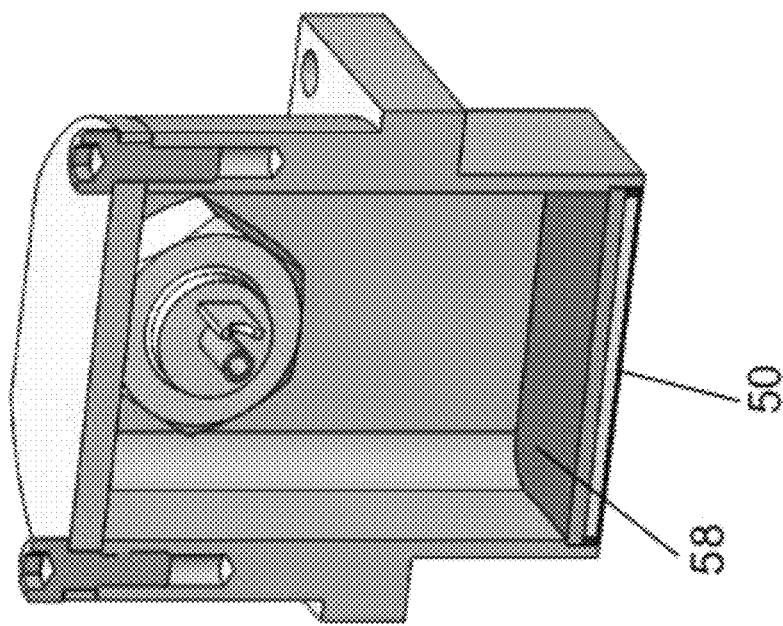
FIG. 17 is a cross-sectional diagram of an ultrasonic transducer of the present disclosure. An air gap is present within the transducer, and a backing layer and wear plate are present.

Screws 88 attach an aluminum top plate 82a of the housing to the body 82b of the housing via threads. The top plate includes a connector 84 for powering the transducer. The top surface of the PZT crystal 86 is connected to a positive electrode 90 and a negative electrode 92, which are separated by an insulating material 94. The electrodes can be made from any conductive material, such as silver or nickel. Electrical power is provided to the PZT crystal 86 through the electrodes on the crystal. Note that the crystal 86 has no backing layer or epoxy layer. Put another way, there is an air gap 87 in the transducer between aluminum top plate 82a and the crystal 86 (i.e. the air gap is completely empty). A minimal backing 58 and/or wear plate 50 may be provided in some embodiments, as seen in FIG. 17.

The transducer design can affect performance of the system. A typical transducer is a layered structure with the ceramic crystal bonded to a backing layer and a wear plate. Because the transducer is loaded with the high mechanical impedance presented by the standing wave, the traditional design guidelines for wear plates, e.g., half wavelength thickness for standing wave applications or quarter wavelength thickness for radiation applications, and manufacturing methods may not be appropriate. Rather, in one embodiment of the present disclosure the transducers, there is no wear plate or backing, allowing the crystal to vibrate in one of its eigenmodes (i.e. near eigenfrequency) with a high Q-factor. The vibrating ceramic crystal/disk is directly exposed to the fluid flowing through the flow chamber.

Removing the backing (e.g. making the crystal air backed) also permits the ceramic crystal to vibrate at higher order modes of vibration with little damping (e.g. higher order modal displacement). In a transducer comprising a crystal with a backing, the crystal vibrates with a more uniform displacement, like a piston. Removing the backing allows the crystal to vibrate in a non-uniform displacement mode. The higher order the mode shape of the crystal, the more nodal lines the crystal may have. The higher order modal displacement of the crystal creates more trapping lines, although the correlation of trapping line to node is not necessarily one to one, and driving the crystal at a higher frequency will not necessarily produce more trapping lines.

In some embodiments, the crystal may have a backing that minimally affects the Q-factor of the crystal (e.g. less than 5%). The backing may be made of a substantially acoustically transparent material such as balsa wood, foam, or cork which allows the crystal to vibrate in a higher order mode shape and maintains a high Q-factor while still providing some mechanical support for the crystal. The backing layer may be a solid, or may be a lattice having holes through the layer, such that the lattice follows the nodes of the vibrating crystal in a particular higher order vibration mode, providing support at node locations while allowing the rest of the crystal to vibrate freely. The goal of the lattice work or acoustically transparent material is to provide support without lowering the Q-factor of the crystal or interfering with the excitation of a particular mode shape.

Placing the crystal in direct contact with the fluid also contributes to the high Q-factor by avoiding the dampening and energy absorption effects of the epoxy layer and the wear plate. Other embodiments may have wear plates or a wear surface to prevent the PZT, which contains lead, contacting the host fluid. Such wear material may be desirable in, for example, biological applications such as separating blood. Such applications might use a wear layer such as chrome, electrolytic nickel, or electroless nickel. Chemical vapor deposition could also be used to apply a layer of poly(p-xylylene) (e.g. Parylene) or other polymers or polymer films. Organic and biocompatible coatings such as silicone or polyurethane are also usable as a wear surface.

Figure 18:
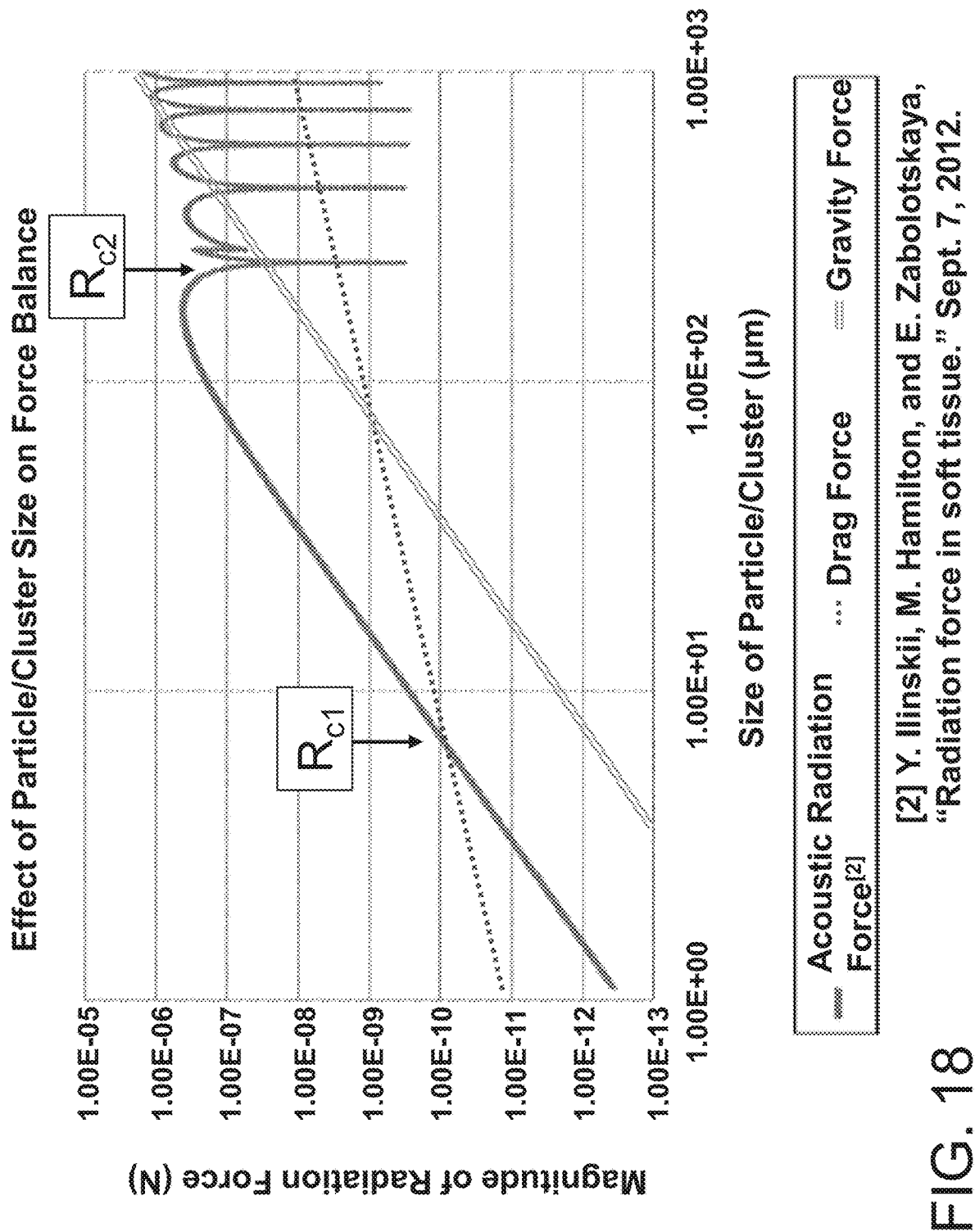
FIG. 18 is a graph showing the relationship of the acoustic radiation force, gravity/buoyancy force, and Stokes' drag force to particle size. The horizontal axis is in microns (μm) and the vertical axis is in Newtons (N).

FIG. 18 is a log-log graph (logarithmic y-axis, logarithmic x-axis) that shows the scaling of the acoustic radiation force, fluid drag force, and buoyancy force with particle radius, and provides an explanation for the separation of particles using acoustic radiation forces. The buoyancy force is a particle volume dependent force, and is therefore negligible for particle sizes on the order of micron, but grows, and becomes significant for particle sizes on the order of hundreds of microns. The fluid drag force (Stokes drag force) scales linearly with fluid velocity, and therefore typically exceeds the buoyancy force for micron sized particles, but is negligible for larger sized particles on the order of hundreds of microns. The acoustic radiation force scaling is different. When the particle size is small, Gor'kov's equation is accurate and the acoustic trapping force scales with the volume of the particle. Eventually, when the particle size grows, the acoustic radiation force no longer increases with the cube of the particle radius, and will rapidly vanish at a certain critical particle size. For further increases of particle size, the radiation force increases again in magnitude but with opposite phase (not shown in the graph). This pattern repeats for increasing particle sizes.

Initially, when a suspension is flowing through the system with primarily small micron sized particles, it is necessary for the acoustic radiation force to balance the combined effect of fluid drag force and buoyancy force for a particle to be trapped in the standing wave. In FIG. 18, this happens at a particle size labeled as $R_{c1}$. The graph then indicates that all larger particles will be trapped as well. Therefore, when small particles are trapped in the standing wave, particles coalescence/clumping/aggregation/agglomeration takes place, resulting in continuous growth of effective particle size. As particles cluster, the total drag on the cluster is much lower than the sum of the drag forces on the individual particles. In essence, as the particles cluster, they shield each other from the fluid flow and reduce the overall drag of the cluster. As the particle cluster size grows, the acoustic radiation force reflects off the cluster, such that the net acoustic radiation force decreases per unit volume. The acoustic lateral forces on the particles may be different than the drag forces for the clusters to remain stationary and grow in size. For example, the acoustic lateral forces may be larger than the drag forces to permit particles to be trapped, cluster and grow in size.

Particle size growth continues until the buoyancy force becomes dominant, which is indicated by a second critical particle size, $R_{c2}$. The buoyancy force per unit volume of the cluster remains constant with cluster size, since it is a function of the particle density, cluster concentration and gravity constant. Therefore, as the cluster size increases, the buoyancy force on the cluster increases faster than the acoustic radiation force. At the size $R_{c2}$, the particles will rise or sink, depending on their relative density with respect to the host fluid. At this size, acoustic forces are secondary, gravity/buoyancy forces become dominant, and the particles naturally drop out or rise out of the host fluid. Not all particles will drop out, and those remaining particles and new particles entering the acoustic chamber will continue to move to the three-dimensional nodal locations, repeating the growth and drop-out process. This phenomenon explains the quick drops and rises in the acoustic radiation force beyond size $R_{c2}$. Thus, FIG. 18 explains how small particles can be trapped continuously in a standing wave, grow into larger particles or clumps, and then eventually will rise or settle out because of increased buoyancy force.

The size, shape, and thickness of the transducer determine the transducer displacement at different frequencies of excitation, which in turn affects particle separation efficiency. Higher order modal displacements generate three-dimensional acoustic standing waves with strong gradients in the acoustic field in all directions, thereby creating equally strong acoustic radiation forces in all directions, leading to multiple trapping lines, where the number of trapping lines correlate with the particular mode shape of the transducer.

FIG. 19 shows the measured electrical impedance amplitude of the transducer as a function of frequency in the vicinity of the 2.2 MHz transducer resonance. The minima in the transducer electrical impedance correspond to acoustic resonances of a water column and represent potential frequencies for operation. Numerical modeling has indicated that the transducer displacement profile varies significantly at these acoustic resonance frequencies, and thereby directly affects the acoustic standing wave and resulting trapping force. Since the transducer operates near its thickness resonance, the displacements of the electrode surfaces are essentially out of phase. The typical displacement of the transducer electrodes is not uniform and varies depending on frequency of excitation. Higher order transducer displacement patterns result in higher trapping forces and multiple stable trapping lines for the captured particles.

To investigate the effect of the transducer displacement profile on acoustic trapping force and particle separation efficiencies, an experiment was repeated ten times, with all conditions identical except for the excitation frequency. Ten consecutive acoustic resonance frequencies, indicated by circled numbers 1-9 and letter A on FIG. 19, were used as excitation frequencies. The conditions were experiment duration of 30 min, a 1000 ppm oil concentration of approximately 5-micron SAE-30 oil droplets, a flow rate of 500 ml/min, and an applied power of 20 W.

As the emulsion passed by the transducer, the trapping lines of oil droplets were observed and characterized. The characterization involved the observation and pattern of the number of trapping lines across the fluid channel, as shown in FIG. 20A, for seven of the ten resonance frequencies identified in FIG. 19.

FIG. 20B shows an isometric view of the system in which the trapping line locations are being determined. FIG. 20C is a view of the system as it appears when looking down the inlet, along arrow 814. FIG. 20D is a view of the system as it appears when looking directly at the transducer face, along arrow 816.

The effect of excitation frequency clearly determines the number of trapping lines, which vary from a single trapping line at the excitation frequency of acoustic resonance 5 and 9, to nine trapping lines for acoustic resonance frequency 4. At other excitation frequencies four or five trapping lines are observed. Different displacement profiles of the transducer can produce different (more) trapping lines in the standing waves, with more gradients in displacement profile generally creating higher trapping forces and more trapping lines. It is noted that although the different trapping line profiles shown in FIG. 20A were obtained at the frequencies shown in FIG. 19, these trapping line profiles can also be obtained at different frequencies.

FIG. 20A shows the different crystal vibration modes possible by driving the crystal to vibrate at different fundamental frequencies of vibration. The 3D mode of vibration of the crystal is carried by the acoustic standing wave across the fluid in the chamber all the way to the reflector and back. The resulting multi-dimensional standing wave can be thought of as containing two components. The first component is a planar out-of-plane motion component (uniform displacement across crystal surface) of the crystal that generates a standing wave, and the second component is a displacement amplitude variation with peaks and valleys occurring in both lateral directions of the crystal surface. Three-dimensional force gradients are generated by the standing wave. These three-dimensional force gradients result in lateral radiation forces that stop and trap the particles with respect to the flow by overcoming the viscous drag force. In addition, the lateral radiation forces are responsible for creating tightly packed clusters of particles. Therefore, particle separation and gravity-driven collection depends on generating a multi-dimensional standing wave that can overcome the particle drag force as the mixture flows through the acoustic standing wave. Multiple particle clusters are formed along trapping lines in the axial direction of the standing wave, as presented schematically in FIG. 20A.

The present disclosure has been described with reference to exemplary embodiments. Modifications and alterations may occur to others upon reading and understanding the preceding detailed description. It is intended that the present disclosure be construed as including all such modifications and alterations insofar as they come within the scope of the appended claims or the equivalents thereof.

The invention claimed is:

1. An acoustophoretic device, comprising:
    an acoustic chamber configured to receive a flow of blood containing blood components;
    an ultrasonic transducer coupled to the acoustic chamber to generate an acoustic wave in an acoustic region of the acoustic chamber;
    a reflector across the acoustic chamber and opposite to the ultrasonic transducer and configured to reflect the acoustic wave to generate an acoustic field in the acoustic region;
    an inlet on a first side of the acoustic chamber;
    a filtrate outlet on a second side of the acoustic chamber, such that the acoustic region is between the inlet and the filtrate outlet;
    a concentrate extraction region below the acoustic region; and
    a lipid collection trap outlet above the acoustic region;
    wherein the acoustic field is configured to concurrently agglomerate blood cells and lipids into clumps that respectively settle towards the concentrate extraction region and rise toward the lipid collection trap outlet.

2. The acoustophoretic device of claim 1, wherein the concentrate extraction region is outside of the acoustic region.

3. The acoustophoretic device of claim 1, wherein the acoustic chamber further comprises an angled wall tapered from the filtrate outlet to the concentrate extraction region.

4. The acoustophoretic device of claim 1, further comprising a container detachably connected to the concentrate extraction region, wherein the container is a disposable bag capable of withstanding temperatures from about −80° C. to about 40° C.

5. The acoustophoretic device of claim 1, wherein the acoustic chamber has an interior volume of at least 50 mL.

6. A portable, autonomous acoustophoretic system comprising:
the acoustophoretic device of claim 1; and
a battery for powering the acoustophoretic device.

* * * * *